(12) United States Patent
Waller et al.

(10) Patent No.: US 7,601,147 B2
(45) Date of Patent: Oct. 13, 2009

(54) CATHETER CONNECTOR ASSEMBLIES AND METHODS FOR ATTACHING A CATHETER AND LUER ASSEMBLY

(75) Inventors: David F. Waller, Winston-Salem, NC (US); Jeremy A. Thomas, Clemmons, NC (US)

(73) Assignee: Winston-Cook Medical Inc., Winston-Salem, NC (US)

( * ) Notice: Subject to any disclaimer, the term of this patent is extended or adjusted under 35 U.S.C. 154(b) by 0 days.

(21) Appl. No.: 11/645,324

(22) Filed: Dec. 22, 2006

(65) Prior Publication Data

US 2007/0167931 A1 Jul. 19, 2007

Related U.S. Application Data

(60) Provisional application No. 60/755,726, filed on Dec. 29, 2005.

(51) Int. Cl.
*A61M 39/10* (2006.01)
*A61M 25/14* (2006.01)
*A61M 31/00* (2006.01)
*A61M 37/00* (2006.01)

(52) U.S. Cl. .............. 604/533; 604/535; 604/93.01

(58) Field of Classification Search ......... 604/533, 604/93.01, 283, 523, 535, 534, 160; 285/332, 285/92, 175, 247
See application file for complete search history.

(56) References Cited

U.S. PATENT DOCUMENTS

| 1,481,341 | A | * | 1/1924 | Bersted | .............. 285/256 |
| 2,191,582 | A | * | 2/1940 | Parker | .............. 285/334.5 |
| 2,269,629 | A | * | 1/1942 | Kreidel | .............. 285/334.4 |
| 2,444,622 | A | * | 7/1948 | Wolfram | .............. 285/332.4 |
| 3,013,310 | A | * | 12/1961 | Done et al. | .............. 264/573 |

(Continued)

FOREIGN PATENT DOCUMENTS

DE 3314640 A1 11/1983

(Continued)

OTHER PUBLICATIONS

Search Report and Written Opinion dated May 5, 2007, for International Application No. PCT/US2006/048798.

(Continued)

*Primary Examiner*—Kevin C Sirmons
*Assistant Examiner*—Michael J Anderson
(74) *Attorney, Agent, or Firm*—Brinks Hofer Gilson & Lione

(57) ABSTRACT

Luer assemblies are provided having first and second connectors operatively coupled and securing tails of a proximal end section of a catheter disposed therebetween. A method for cutting a proximal end section of a catheter having distal and proximal ends is provided, a slit in the proximal end section exposing a catheter lumen and forming first and second tails having inner, outer, and peripheral engaging surfaces. Another method secures catheter tails disposed between operatively coupled first and second connectors, the first connector having a distal insert inserted into the exposed catheter lumen and a catheter engaging body about which the catheter tails are disposed, and the second connector having a catheter engaging body disposed about the catheter tails, wherein the connectors are configured to be operatively coupled to each other and to operatively couple the catheter tails disposed between the catheter engaging bodies of the first and second connectors.

17 Claims, 15 Drawing Sheets

U.S. PATENT DOCUMENTS

| | | | | |
|---|---|---|---|---|
| 3,441,296 A * | 4/1969 | Wilkin | | 285/148.13 |
| 3,469,579 A * | 9/1969 | Hubert | | 604/533 |
| 3,720,210 A * | 3/1973 | Diettrich | | 604/533 |
| 3,833,246 A * | 9/1974 | Wake | | 285/247 |
| 3,843,169 A * | 10/1974 | Wise | | 285/39 |
| 4,033,613 A * | 7/1977 | Bram | | 285/184 |
| 4,128,264 A * | 12/1978 | Oldford | | 285/41 |
| 4,152,817 A * | 5/1979 | Cotten | | 29/890.14 |
| 4,452,473 A | 6/1984 | Ruschke | | |
| 4,500,118 A * | 2/1985 | Blenkush | | 285/247 |
| 4,619,644 A * | 10/1986 | Scott | | 604/506 |
| 4,629,455 A | 12/1986 | Kanno | | |
| 4,735,441 A | 4/1988 | Stephens | | |
| 4,735,442 A * | 4/1988 | Burli | | 285/148.13 |
| 4,929,236 A * | 5/1990 | Sampson | | 604/175 |
| 4,951,976 A * | 8/1990 | Boelkins | | 285/114 |
| 4,963,133 A * | 10/1990 | Whipple | | 604/533 |
| 5,047,021 A | 9/1991 | Utterberg | | |
| 5,120,084 A * | 6/1992 | Hashimoto | | 285/133.11 |
| 5,129,891 A * | 7/1992 | Young | | 604/533 |
| 5,160,325 A * | 11/1992 | Nichols et al. | | 604/247 |
| 5,176,415 A | 1/1993 | Choksi | | |
| 5,188,605 A * | 2/1993 | Sleep | | 604/158 |
| 5,286,067 A | 2/1994 | Choksi | | |
| 5,312,337 A * | 5/1994 | Flaherty et al. | | 285/278 |
| 5,364,135 A * | 11/1994 | Anderson | | 285/38 |
| 5,387,192 A * | 2/1995 | Glantz et al. | | 604/288.02 |
| 5,405,340 A * | 4/1995 | Fageol et al. | | 604/533 |
| 5,529,349 A * | 6/1996 | Gibbs et al. | | 285/332 |
| 5,549,583 A | 8/1996 | Sanford et al. | | |
| 5,611,576 A | 3/1997 | Guala | | |
| 5,613,945 A * | 3/1997 | Cai et al. | | 604/288.02 |
| 5,620,427 A | 4/1997 | Werschmidt et al. | | |
| 5,632,729 A * | 5/1997 | Cai et al. | | 604/288.01 |
| 5,651,776 A | 7/1997 | Appling et al. | | |
| 5,658,262 A * | 8/1997 | Castaneda et al. | | 604/264 |
| 5,702,374 A | 12/1997 | Johnson | | |
| 5,743,873 A * | 4/1998 | Cai et al. | | 604/288.02 |
| 5,782,505 A * | 7/1998 | Brooks et al. | | 285/148.19 |
| 5,895,695 A * | 4/1999 | Rowley | | 428/36.9 |
| 5,928,208 A * | 7/1999 | Chu et al. | | 604/523 |
| 5,967,569 A * | 10/1999 | Vaillancourt et al. | | 285/295.2 |
| 5,984,373 A | 11/1999 | Fitoussi et al. | | |
| 6,042,577 A * | 3/2000 | Chu et al. | | 604/523 |
| 6,045,162 A * | 4/2000 | Haibara | | 285/55 |
| 6,113,572 A * | 9/2000 | Gailey et al. | | 604/93.01 |
| 6,251,119 B1 * | 6/2001 | Addis | | 606/167 |
| 6,287,501 B1 * | 9/2001 | Rowley | | 264/254 |
| 6,332,633 B1 | 12/2001 | Fitoussi et al. | | |
| 6,344,033 B1 | 2/2002 | Jepson et al. | | |
| 6,402,207 B1 | 6/2002 | Segal et al. | | |
| 6,557,907 B2 * | 5/2003 | Rowley | | 285/354 |
| 6,638,242 B2 * | 10/2003 | Wilson et al. | | 604/43 |
| 6,673,059 B2 * | 1/2004 | Guala | | 604/533 |
| 6,860,524 B1 * | 3/2005 | Rowley | | 285/354 |
| 6,921,396 B1 * | 7/2005 | Wilson et al. | | 604/508 |
| 6,939,327 B2 * | 9/2005 | Hall et al. | | 604/164.05 |
| 7,128,348 B2 * | 10/2006 | Kawamura et al. | | 285/332 |
| 7,163,531 B2 * | 1/2007 | Seese et al. | | 604/533 |
| 2003/0097091 A1 * | 5/2003 | Hobbs et al. | | 604/43 |
| 2003/0163139 A1 * | 8/2003 | Graf | | 606/108 |
| 2004/0030319 A1 * | 2/2004 | Korkor et al. | | 604/506 |
| 2004/0034324 A1 * | 2/2004 | Seese et al. | | 604/246 |
| 2004/0054321 A1 * | 3/2004 | Schon et al. | | 604/93.01 |
| 2004/0254534 A1 * | 12/2004 | Bjorkman et al. | | 604/160 |
| 2005/0010238 A1 * | 1/2005 | Potter et al. | | 606/129 |
| 2005/0090779 A1 * | 4/2005 | Osypka | | 604/160 |
| 2005/0096585 A1 * | 5/2005 | Schon et al. | | 604/43 |
| 2005/0099004 A1 * | 5/2005 | Bouey et al. | | 285/249 |
| 2005/0182387 A1 * | 8/2005 | Webler | | 604/527 |
| 2005/0256461 A1 * | 11/2005 | DiFiore et al. | | 604/247 |
| 2005/0256508 A1 * | 11/2005 | Hall | | 604/529 |
| 2005/0261636 A1 * | 11/2005 | Rome et al. | | 604/247 |
| 2005/0261663 A1 * | 11/2005 | Patterson et al. | | 604/508 |
| 2006/0030864 A1 * | 2/2006 | Kennedy, et al. | | 606/108 |
| 2006/0259012 A1 * | 11/2006 | Propp et al. | | 604/533 |
| 2006/0284421 A1 * | 12/2006 | Fonville et al. | | 285/386 |

FOREIGN PATENT DOCUMENTS

| FR | 2 703593 A1 | 10/1994 |
|---|---|---|
| WO | WO 2007/005584 | 1/2007 |
| WO | WO 2007/005584 A1 | 1/2007 |

OTHER PUBLICATIONS

International Search Report mailed Jul. 10, 2008, for International Application No. PCT/US2006/048798.

* cited by examiner

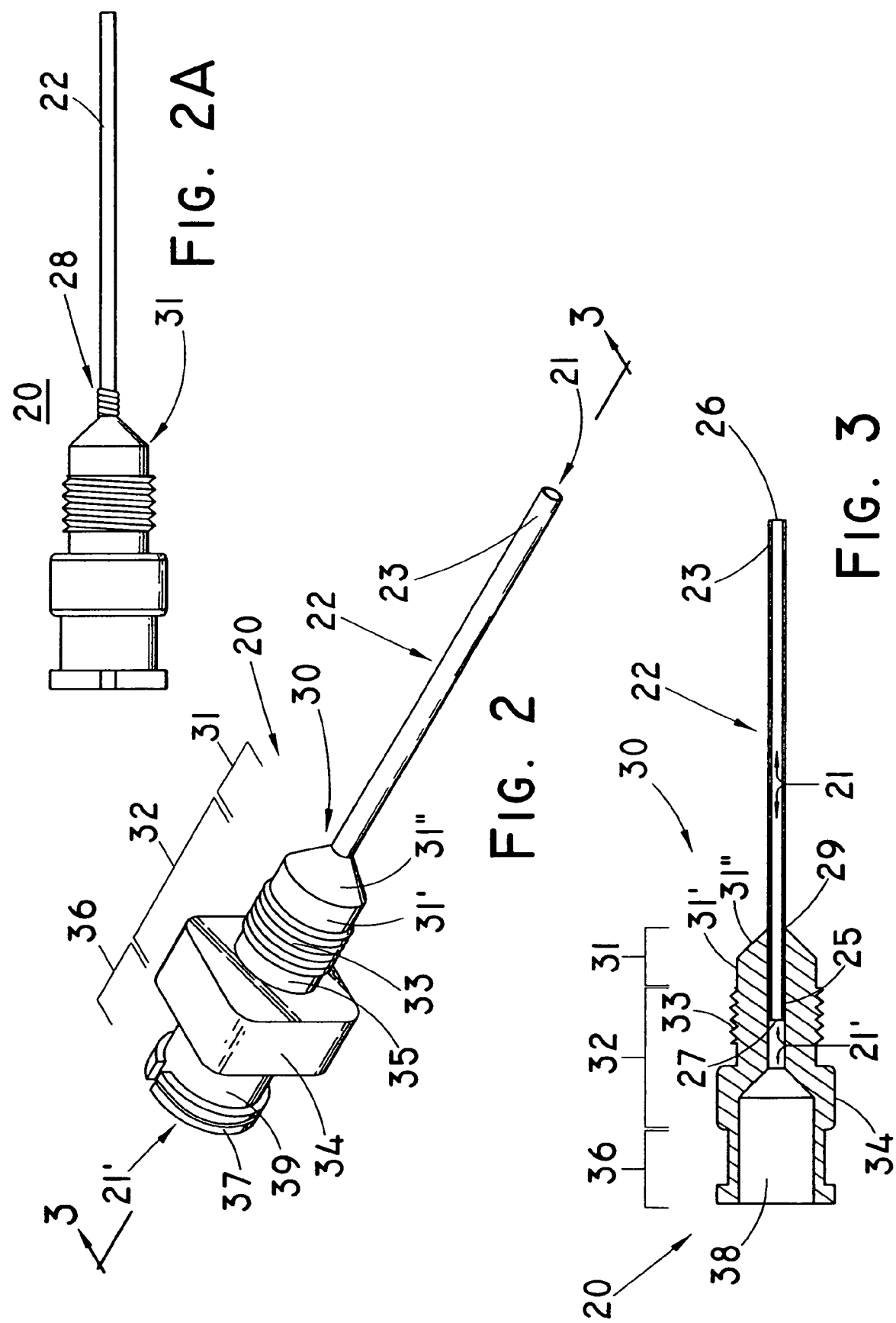

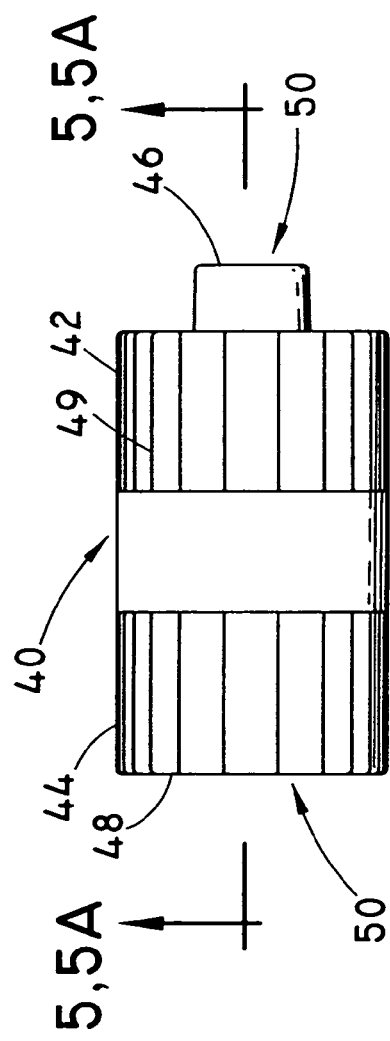
FIG. 4
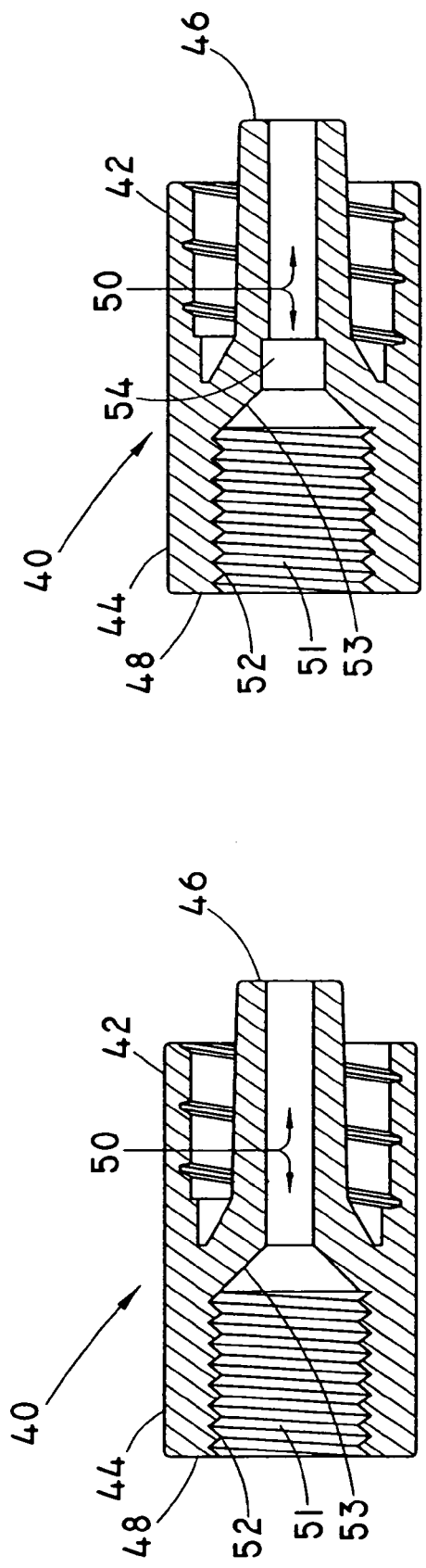
FIG. 5A
FIG. 5

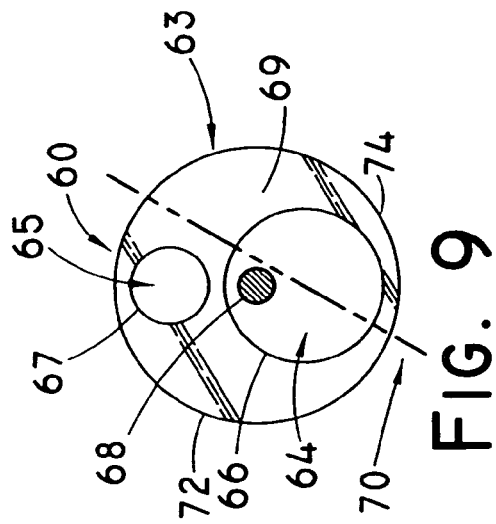
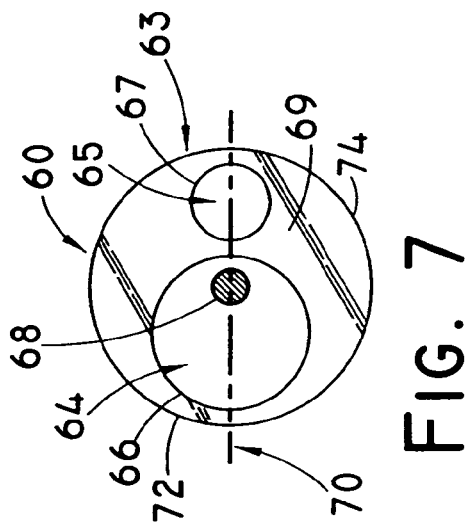
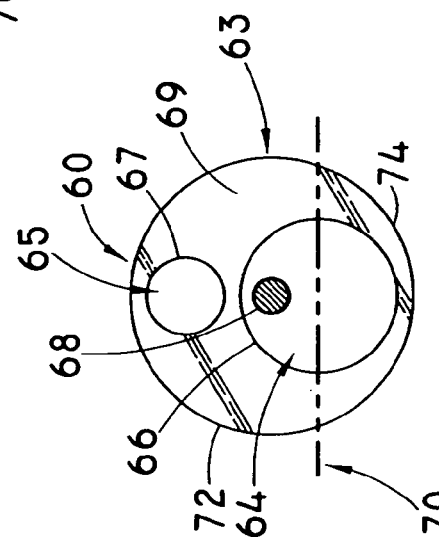
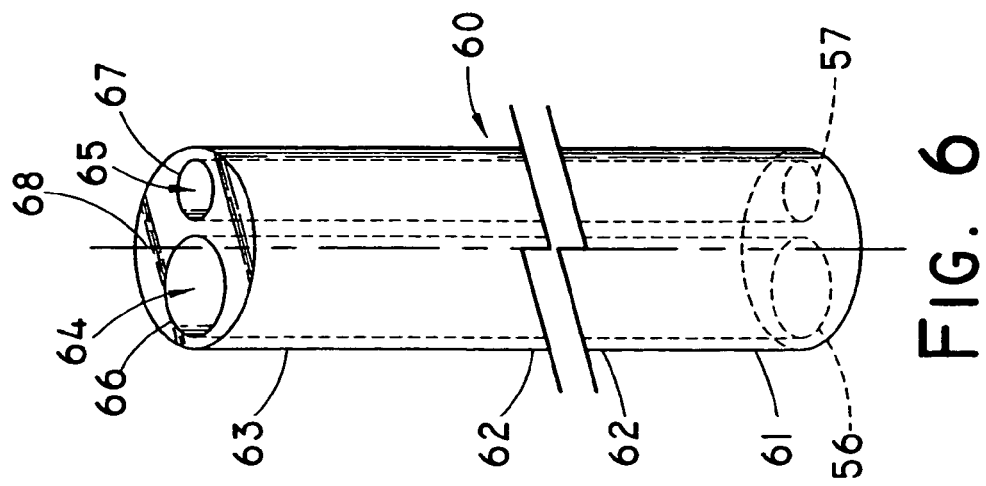

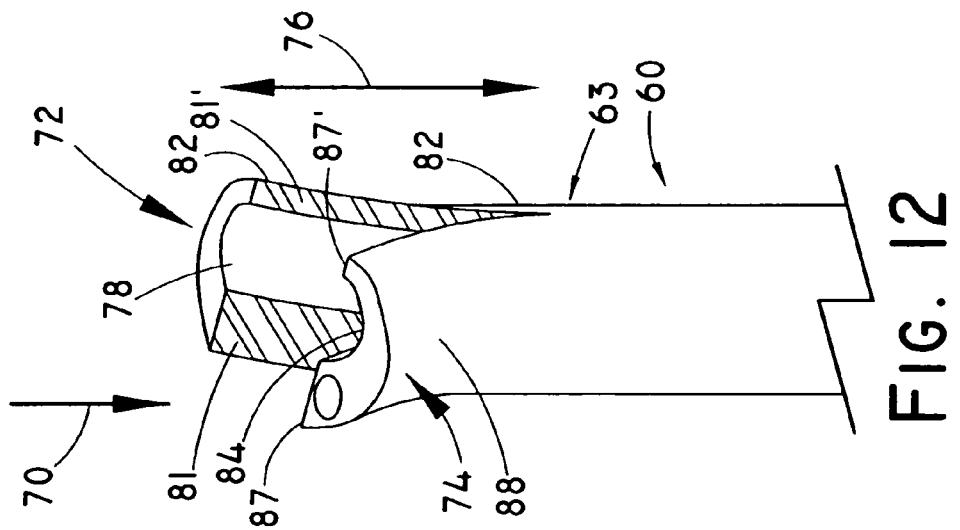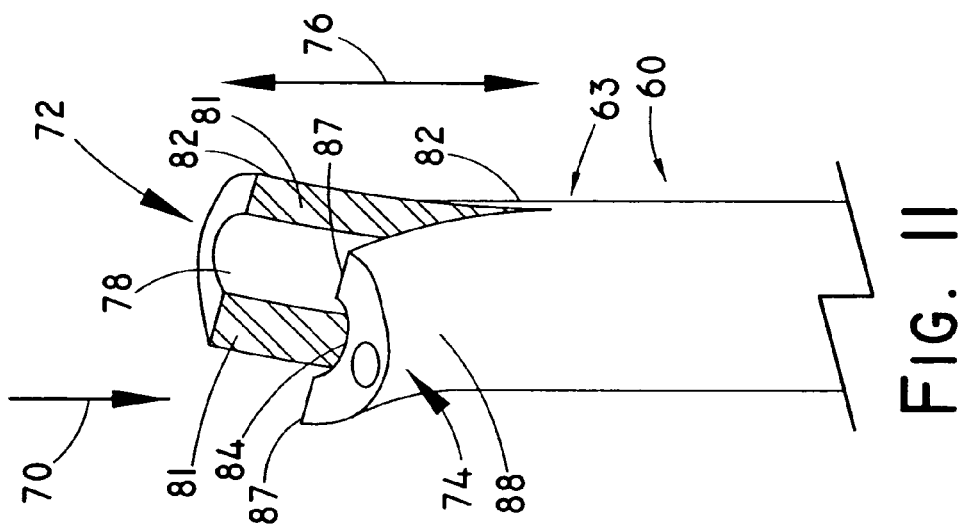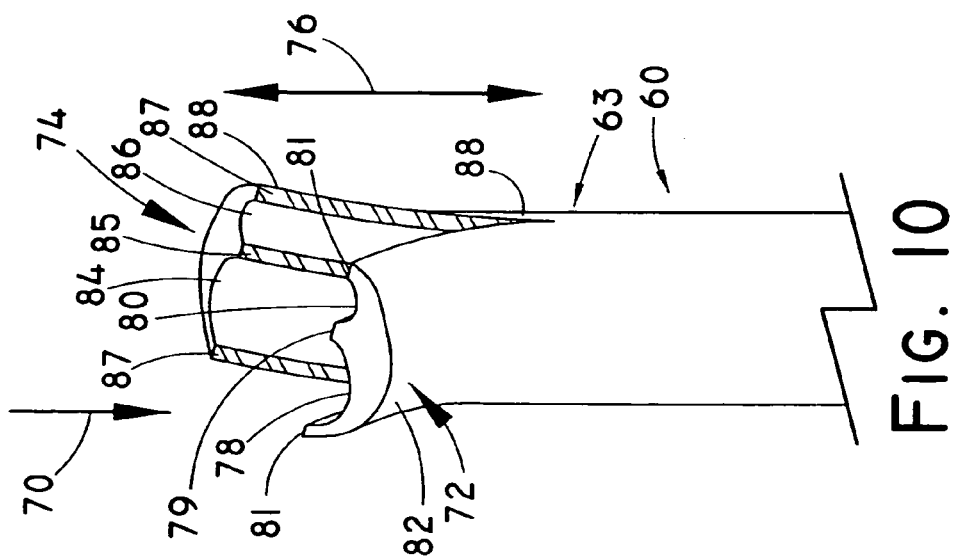

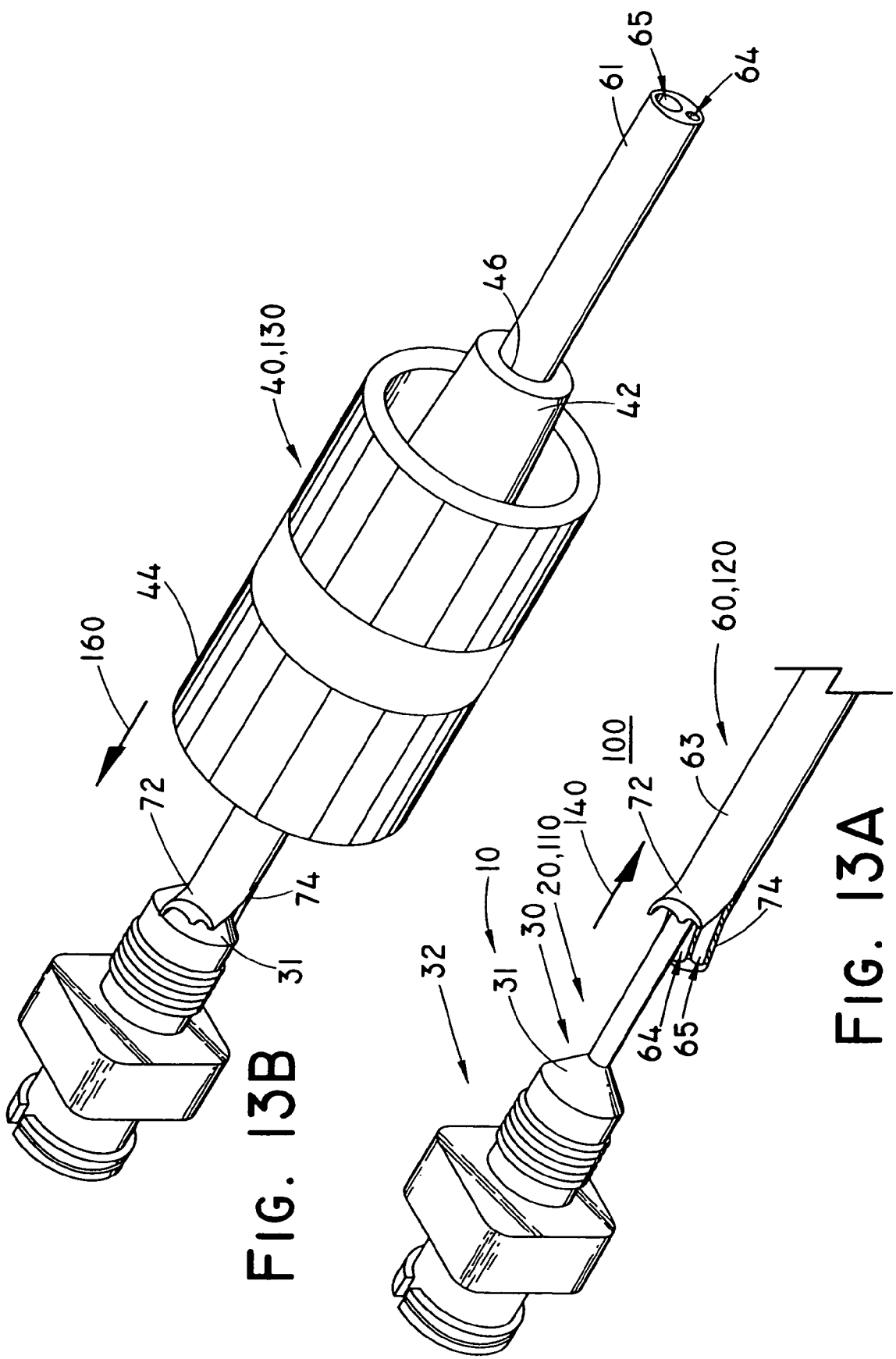

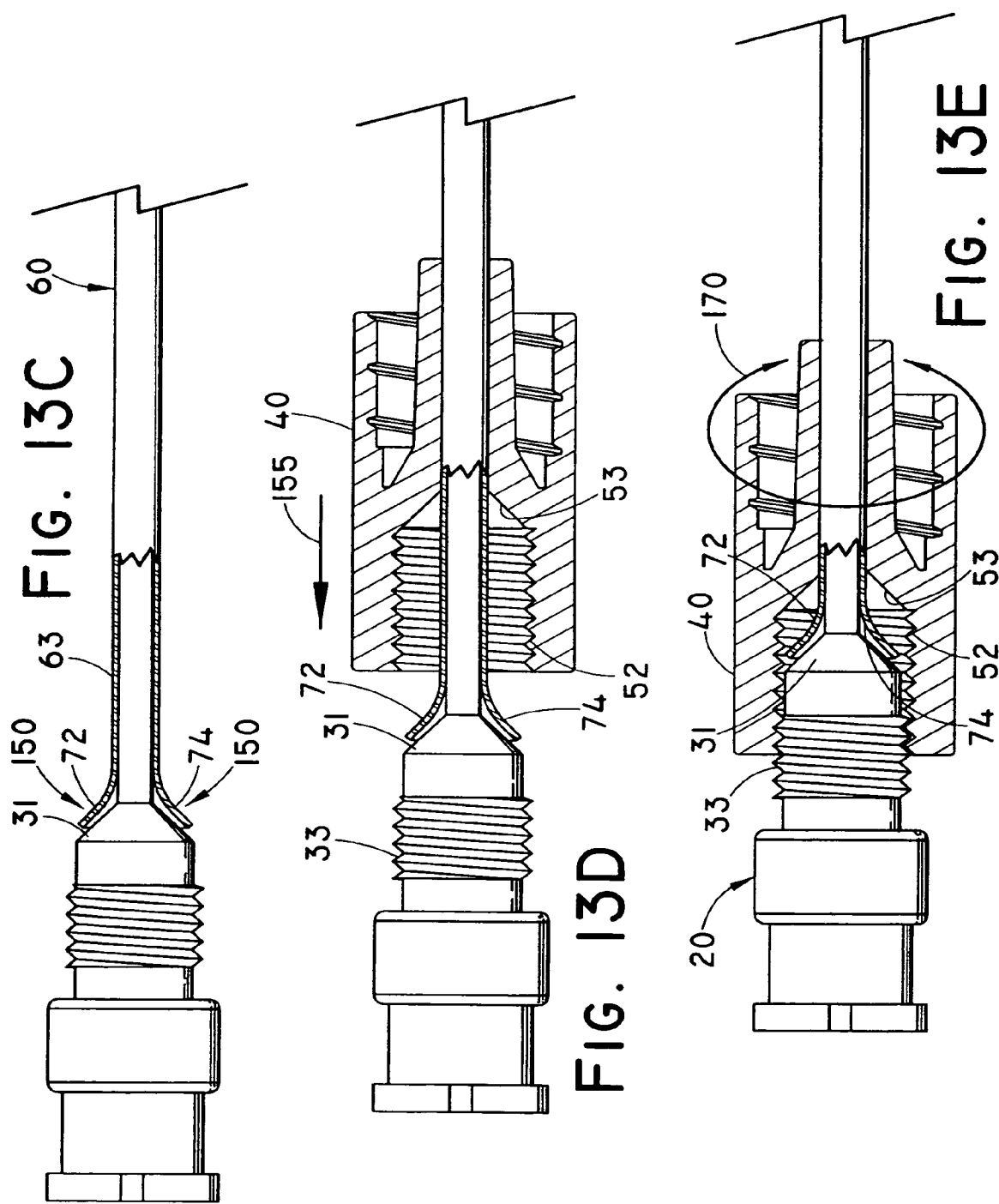

CATHETER CONNECTOR ASSEMBLIES AND METHODS FOR ATTACHING A CATHETER AND LUER ASSEMBLY

RELATED APPLICATIONS

The present patent document claims the benefit of the filing date under 35 U.S.C. §119(e) of U.S. Provisional Patent Application filed on Dec. 29, 2005 entitled, "Catheter Connector Assemblies And Methods For Attaching A Catheter And Luer Assembly," and having an application Ser. No. 60/755,726, the disclosure of which is hereby incorporated by reference in its entirety.

TECHNICAL FIELD

The present invention relates to catheter connector assemblies and methods for attaching a catheter and a luer assembly. More particularly, the invention involves an apparatus and a method for slitting a proximal end portion of a catheter and attaching the proximal catheter slit end portion to first and second connectors. Still more particularly, the first and second connectors are configured for operatively coupling to each other and to the tails formed at the catheter proximal slit end portion are operatively coupled therebetween.

BACKGROUND OF THE INVENTION

Conventionally, physicians, gastroenterologists, or other healthcare professionals ("physician(s)") utilize luer assemblies for quickly, securely, and reliably connecting medical devices to be used in many medical or surgical applications. For instance, physicians use luer assemblies to connect syringes at one end and catheters at the other end in order to form fluid flow conduits from the syringe to the catheter and the catheter into a body passageway within a patient.

The term "passageway" is understood to be any lumen, chamber, channel, conduit, opening, bore, orifice, flow passage, duct, or cavity configured for allowing the conveyance, regulation, flow, or movement of fluids, liquids, and/or gases such as, by way of example and not by way of limitation, bodily fluids and/or gases of or to an animal. As an example, devices utilizing luer assemblies and catheters have become widely accepted in the medical field for use in the passageways of an aorta, artery, bile duct, blood vessel, bronchiole, capillary, colon, esophagus, fallopian tube, gastroduodenal, gastroesophageal, gastrointestinal, heart, intestine, pylorus, trachea, ureter, urethra, vein, and other locations in a body (collectively, "vessel") to name a few.

In order to further provide a background of the invention, catheters will be discussed next. Then, syringes will be discussed. Following the discussion on catheters and syringes, an overview of luer assemblies will be reviewed as a background of the invention. These components are only provided for background purposes, and not as limitations of the invention.

Catheter

A catheter, in general terms, is a tubular device having proximal and distal ends with openings at or near those ends and defining a lumen. As is conventional, the term "distal" means away from the physician when the catheter is being or has already been inserted into a patient, while the term "proximal" means closest to or toward the physician when the catheter is being or has already been inserted into a patient. Catheters may have one lumen (e.g., a single-lumen catheter) or more than one lumen (e.g., a multi-lumen catheter) such as, by way of example only, two lumens. In order to accommodate most of its medical uses, the catheter generally can fall into two categories: a thin, flexible tube (a "soft" catheter) or a larger, solid tube (a "hard" catheter).

The process whereby the physician inserts a catheter is commonly known as catheterization. The catheter lumen allows fluids to enter or, as desired, exit a vessel passageway within a patient. What is commonly known as a central line, for example, is a catheter assembly that provides a conduit for delivering drugs or fluids to a large-bore catheter positioned either in a vein near the heart or just inside the atrium of the patient. Likewise, the catheter lumen may allow gases to pass into the vessel passageway, such as to distend the vessel for surgery, either directly through the catheter lumen or through intervening parts or devices associated with the catheter.

Catheterization has many other medical and surgical applications in addition to the central line assembly and those mentioned above. By way of example only and not by way of limitation, placing a catheter into a particular vessel passageway may facilitate many medical procedures: (1) draining urine from the urinary bladder as in urinary catheterization (i.e., a Foley Catheter) or even when the urethra is damaged as in the procedure known as super-pubic catheterization; (2) administering intravenous fluids, medication, or parenteral nutrition; (3) practicing angioplasty in order to unblock a blood vessel or artery; (4) injecting dye or radio-opaque contrast into blood vessels or other structures to visualize abnormalities, as in cardiac catheterization, which is part of coronary angiography; (5) directly measuring blood pressure in an artery or a vein; (6) infusing local anesthetics and other drugs for epidural anesthesia; and (7) suctioning unwanted fluids from the airway (usually with a hard catheter).

Syringe

An optional syringe may be used directly or indirectly with a luer assembly (discussed below) for carrying or removing fluids, liquids, and/or gases such as, by way of example and not by way of limitation, intravenous fluids, blood, medications, and/or gases. A typical syringe comprises a plunger fitted to a proximal end of a tube, called the barrel, the barrel having a small opening at or near its distal end. The barrel of a syringe may be made of plastic or glass and usually has graduated marks indicating a volume of fluid and/or gases in the syringe.

While glass syringes may be sterilized by the use of an autoclave, modern medical syringes are typically made from plastic. Disposing plastic syringes tends to be more cost-effective than sterilizing glass syringes. Also, disposing plastic syringes in lieu of sterilizing glass syringes may reduce the risk of spreading blood-borne diseases.

Physicians use syringes to transfer or remove liquids or gases to or from otherwise inaccessible areas within a patient. Syringes operate on the principle of negative pressure (e.g., suction) being used to fill the barrel with a substance at the syringe's distal opening as the physician draws out the plunger, and expelling the substance when the physician depresses the plunger. The process of administering a substance with a syringe and needle is called an injection.

Luer Assembly

Luer connectors, luer type fittings, and other medical connector systems (individually and collectively, "luer assemblies") provide fluid flow conduits for use in medical or surgical applications. These luer assemblies may come in many types. Generally stated, luer assemblies include a male member and female member configured to be joined together, each member configured to have proximal and distal ends with openings and each defining a lumen therethrough such that the physician may connect the male and female members directly or indirectly through intervening parts. Typically, though not always, the male member has a slightly tapered distal body designed for inserting into the female member, and the female member has a similarly tapered bore for receiving the male member.

One luer assembly for instance, commonly called a luer slip, comprises a friction fit between a tapered distal end of a male member that has been inserted into a corresponding tapered proximal bore within a female member. Another illustrative type of luer assembly, commonly called a luer lock connection, includes a female luer distal end with an annular flange having internal threads and a male luer proximal end with a threaded outer surface for engaging the female threads. Alternatively, the male member has a distal end with a flange, protrusion, or rib for interlocking with a corresponding flange, recess, or rib at or near the proximal end of the female member.

The luer assembly may also comprise an optional collar to help join the male and female members. For instance, the optional collar might comprise internal threads to mount the female luer member and maintain the connection between the male and female members and substantially prevent fluid leakage between the male and female members. The collar threads might draw the male and female members together or otherwise engage corresponding threads in one or both of the male or female members. With one design, the physician rotates the collar about the male and female members by hand.

In addition, the male luer member may have an optional distal catheter hub for securing an optional cannula. Generally stated, the optional cannula is a tube that, when inserted into the body of a patient directly—or indirectly by inserting into a lumen of a catheter that in turn is inserted into the body of a patient directly—is typically used either to withdraw fluid or insert medication. If inserted directly into the patient, the optional cannula normally comes with a trocar (a sharp pointed needle-like device) attached to the cannula's distal end for puncturing the dermis of a patient in order to be used percutaneously at the intended space. When a cannula is attached to a distal end of a male luer member and is intended to be inserted into a catheter, then the cannula may be rigid, flexible, or partially flexible and configured without the trocar (or with a less sharp trocar) so as not to puncture the catheter inner walls upon insertion into the catheter lumen. Furthermore, the male luer member optionally may have a proximal syringe hub for joining to a syringe.

Luer assemblies are well known in the medical device field. Indeed, luer assemblies are ubiquitous in hospitals where they commonly, for example, connect a syringe outside the patient with a catheter inserted, or intended to be inserted, within the patient's vessel passageway.

Typical procedures for using luer assemblies with catheters, however, currently are limited by the variable of whether the catheter is a single lumen catheter or a multi-lumen (e.g., two or more lumens) catheter. When the catheter has a single lumen, conventional methods comprise steps that require the catheter proximal end to be flared so as to mate with the tapered distal end of the luer assembly. In order to expand or otherwise open the catheter proximal end outwardly, an iron rod typically is inserted into the catheter lumen, wherein the iron rod is heated before or after insertion into the catheter lumen. One problem with using the flaring rod to flare the catheter proximal end, however, is that, if too much heat is used or for too long, the catheter may burn or degrade. In addition, the catheter lumen needs to be sized for the iron rod, so the physician may need to keep on hand many iron rods of different sizes.

The present invention solves these and other problems by providing a select slit at a catheter proximal end portion of a single lumen catheter through the catheter lumen in order to form tails at the proximal end portion. The tails are disposed between operatively coupled first and second connectors.

With a multi-lumen catheter, a cannula secured to the male member distal end typically inserts into one lumen with an interference fit and thereby centers the male member relative to that lumen. This procedure for attaching the catheter and luer assembly provides for easy assembly, but often has compromised joint integrity whereby the luer connection can loosen and possibly even disconnect. Where the joint integrity fails totally or even in part, fluid leakage may result and, in some cases, disrupt the flow from the syringe (or other fluid container located at the luer assembly proximal hub) to the patient at the luer assembly distal end. Accordingly, there is a need to provide a method for attaching catheters and luer assemblies that allows for strong joint strength to multi-lumen catheters.

The present invention solves these and other problems by providing a select slit at the proximal end portion of the multi-lumen catheter through one or more of the lumens in order to form tails. The tails are disposed between operatively coupled first and second connectors.

In addition to providing strong joint strength, these novel methods and catheter connector assemblies as taught herein have the added benefit of being used with readily available luer assemblies and catheters with which physicians are already familiar. Also, when operatively coupled between the first and second connectors, the tails provide a quick connect/disconnect, joint integrity, and sealing properties.

SUMMARY OF THE INVENTION

The present invention provides a catheter assembly. In particular, the present invention provides a catheter having a distal end portion, an elongate middle portion, a proximal end portion, and a lumen extending from the proximal end portion to or near the distal end portion. The catheter proximal end portion has a slit forming a first tail and a second tail. Also provided are operatively coupled first and second connectors, wherein the catheter tails are disposed therebetween.

Methods for attaching a catheter are also provided. In one embodiment, the method includes providing a first connector and a second connector configured to be operatively coupled, the first connector includes a distal insert section having a lumen and a connector section having a catheter engaging body and an actuation body, and the second connector having a catheter engaging body. A catheter is provided having a distal end portion, an elongate middle portion, a proximal end portion, and a lumen extending from the proximal end portion to or near the distal end portion, wherein the catheter proximal end portion has a slit forming a first tail and a second tail. The first connector distal insert section is inserted into the catheter lumen exposed by the slit, and the catheter tails are disposed about the first connector catheter engaging body. The first and second connectors are operatively coupling such that the catheter tails are secured between the first connector catheter engaging body and the second connector catheter engaging body.

In another embodiment of a method according to the invention, a method for cutting a catheter is provided. The method includes providing a cutting tool, a catheter locking member, and a catheter. The catheter has a distal end portion, an elongate middle portion, a proximal end portion, and a lumen extending from the proximal end portion to or near the distal end portion. The catheter proximal end portion is secured to the catheter locking member and the catheter lumen is cut with the cutting tool at the catheter proximal end portion, the cutting step forming a slit in the catheter proximal end portion, which slit exposes the catheter lumen and forms a first tail and second tail, each tail having an inner engaging surface, an outer engaging surface, and at least one peripheral engaging surface at the catheter proximal end portion.

BRIEF DESCRIPTION OF THE DRAWINGS

FIG. 2 shows a perspective view of one embodiment of a first connector according to the present invention.

FIG. 2A shows a perspective view of an alternative embodiment of a first connector according to the present invention.

FIG. 3 shows a longitudinal, sectional view of one embodiment of the first connector of FIG. 2 taken along the lines 3-3.

FIG. 4 shows a perspective view of one embodiment of a second connector according to the present invention.

FIG. 5 shows a longitudinal, sectional side view of FIG. 4 taken along the lines 5-5.

FIG. 5A shows a longitudinal, sectional side view of an alternative embodiment of a second connector according to FIG. 4 taken along the lines 5A-5A for use with an alternative embodiment of a first connector according to FIG. 2A.

FIG. 6 shows a perspective view, broken away, of one embodiment of a catheter.

FIG. 7 is a schematic end-on view showing an embodiment of a slit to be made at a proximal end portion of a catheter according to the present invention.

FIG. 8 is a schematic end-on view showing an alternative embodiment of a slit to be made at a proximal end portion of a catheter according to the present invention.

FIG. 9 is a schematic end-on view showing another embodiment of a slit to be made at a proximal end portion of a catheter according to the present invention.

FIG. 10 is a perspective view of the catheter of FIG. 7 showing an embodiment of a slit proximal end of a catheter according to the present invention.

FIG. 11 is a perspective view of the catheter of FIG. 8 showing an alternative embodiment of a slit proximal end of a catheter according to the present invention.

FIG. 12 is a perspective view of the catheter of FIG. 9 showing another embodiment of a slit proximal end of a catheter according to the present invention.

FIG. 13A shows steps of the method according to FIG. 13 wherein a first connector and a catheter are provided and the first connector distal insert is inserted a lumen exposed by a slit forming catheter tails at the catheter proximal end portion.

FIG. 13B shows a step of the method according to FIG. 13 wherein a second connector is provided and moved into position by inserting a distal end portion of the catheter of FIG. 13A through the second connector and sliding the second connector proximally over the catheter toward the catheter proximal end portion and first connector.

FIG. 13C shows a partial sectional view, broken away of catheter tails of a proximal end section of a catheter according to one embodiment of the invention being disposed about a first connector catheter engaging body.

FIG. 13D shows a partial sectional view, broken away of first and second connectors and catheter tails according to a step of a method of the invention wherein the first and second connectors of FIGS. 13A and 13B are operatively coupled such as by a first connector fastener and a second connector fastener.

FIG. 13E shows a step of the method according to FIG. 13 wherein the first and second connectors of FIGS. 13A and 13B are operatively coupled such as by rotating the second connector into engagement with the first connector.

DESCRIPTION OF THE INVENTION

The present invention relates to catheter connector assemblies and methods for attaching a catheter and a luer assembly. More particularly, the invention involves an apparatus and a method for slitting a proximal end portion of a catheter and attaching the proximal catheter slit end portion to first and second connectors. Still more particularly, the first and second connectors are configured for operatively coupling to each other, and to the tails formed at the catheter proximal slit end portion are operatively coupled therebetween.

The terms "operatively coupling," "operatively coupled," "coupling," "coupled," and variants thereof are not used lexicographically but instead are used to describe embodiments of the invention having a point, position, area, volume, or configuration at which two or more things are directly or indirectly—as through intervening parts—detachably or substantially fixedly joined, adjoined, connected, associated, united, mated, interlocked, conjoined, fastened, held together, clamped, crimped, sandwiched, viced, engaged, friction fitted, press fitted, and/or wedged directly or indirectly together or held together by a crimp sleeve. The present invention also relates to a method for cutting a catheter proximal end portion such that the first and second connectors may operatively couple the catheter proximal end portion therebetween.

For the purpose of promoting an understanding of the principles of the invention, the following provides a detailed description of embodiments of the invention as illustrated by the drawings as well as the language used herein to describe various aspects of the invention. The description is not intended to limit the invention in any manner, but rather serves to enable those skilled in the art to make and use the invention. As used herein, the terms comprise(s), include(s), having, has, with, contain(s) and variants thereof are intended to be open ended transitional phrases, terms, or words that do not preclude the possibility of additional steps or structure.

Figure 1:
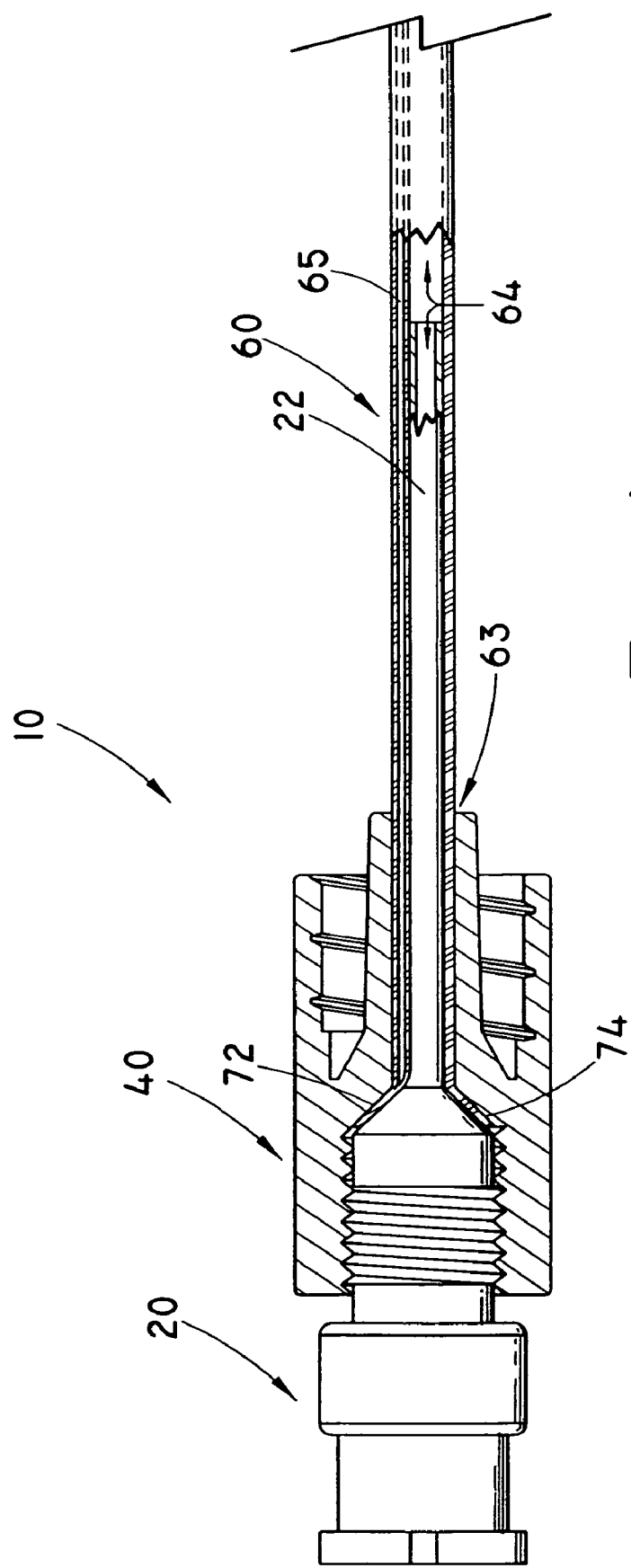
FIG. 1 is a schematic illustration, broken away and partially sectioned, of an assembly having a first connector, a second connector, and a catheter operatively coupled according to one embodiment of the present invention.

FIG. 1 shows a schematic illustration, broken away and partially sectioned, of a luer assembly 10 according to one embodiment of the present invention. The luer assembly 10 comprises a catheter 60 having at least one lumen as in a single lumen catheter or in one embodiment having a plurality (more than one) lumens as in a multi-lumen catheter. By way of example only and not by way of limitation, FIG. 1 shows a catheter 60 having a first lumen 64 and a second lumen 65. As more fully described below (FIG. 6), a catheter 60 is elongate (long) and comprises a distal first end 61 and a proximal second end section 63.

According to an embodiment of the invention as illustrated in FIG. 1, in addition to a single or multi-lumen catheter 60, the luer assembly 10 comprises a first connector 20 having a catheter engaging body 31 (e.g., FIG. 2) and a lumen 21' extending therethrough (e.g., FIG. 3). The first connector 20 may further comprise an optional distal insert 22 having a lumen 21, which distal insert 22 is at least partially inserted into at least a portion of the catheter first lumen 64, wherein the distal insert lumen 21 is in fluid communication with the first connector lumen 21'. The luer assembly 10 also comprises a second connector 40. The first and second connectors 20, 40, respectively, are operatively coupled to each other and a first tail 72 and a second tail 74 of the proximal second end section 63 of the single or multi-lumen catheter 60.

FIG. 2 shows a perspective view of one embodiment of a first connector 20 according to the invention. The first connector 20 comprises a distal insert 22 and a proximal connector section 30, the connector section 30 including said first connector lumen 21' and being more fully described below. The distal insert 22 and proximal connector section 30 may be substantially rigid and may be made of any suitable material (natural, synthetic, plastic, rubber, metal, or combination thereof), although the distal insert 22 may have some flexibility as explained below. In one embodiment, the first connector 20 comprises a male luer fitting connector.

In an embodiment wherein the catheter 60 has one lumen only (i.e., a single lumen catheter), the first connector distal insert 22 is optional. The catheter first tail 72 and catheter second tail 74 are substantially self-centering about at least a portion of the proximal connector section (e.g., a catheter engaging body 31) without the need for inserting a distal insert 22 (e.g., a cannula attached to the connector section 30) and within either the catheter first lumen 64 or the catheter second lumen 65.

Where the luer assembly 10 has a distal insert 22 and a proximal connector section 30, the first connector 20 comprises the distal insert 22 having a lumen 21 and further comprises a proximal connector section 30 wherein said first connector lumen 21' extends therethrough and is in fluid communication with the distal insert lumen 21 (FIG. 3). The term "fluid communication" and variants thereof are not used lexicographically but instead are used to describe embodiments of the invention such that the lumens 21, 21' are configured to allow conveyance, regulation, flow, and/or movement of fluids, medication, and/or gases therethrough. Alternatively, and in accordance with another aspect of the invention, the lumens 21, 21' can be separated by additional intervening spacings, passageways, and/or occlusions, bushings, diaphragm seals, and/or valves (and/or valve/diaphragm seal equivalents) configured to open/close and otherwise allow fluid communication of the lumens 21, 21'.

One embodiment of the distal insert 22 comprises a tubular structure having a distal first end 23 (see FIGS. 2 and 3) configured to be inserted into one of a first catheter lumen 64 or a second catheter lumen 65 (see FIG. 1). In one embodiment, the distal insert 22 is a hollow cannula. The distal insert 22 may be substantially rigid or semi-rigid (i.e., partially flexible). For example, the distal first end 23 may be semi-rigid while a proximal second end 25 (see FIG. 3) may be rigid. To the extent that the distal first end 23 may be inserted into a catheter lumen without significant prolapse of the distal first end 23, the distal first end 23 may even be substantially flexible. The distal insert 22 may be any suitable length. In one embodiment, the distal insert 22 is approximately 1.682 inches in length, although it may be longer or shorter as desired. Likewise, the lumen 21 may be any suitable diameter. In one embodiment, the lumen 21 is approximately 0.035 inches in diameter, although it may be wider or narrower as desired.

In FIG. 2, the first connector 20 also comprises a proximal connector section 30. The connector section 30 includes a catheter engaging body 31, which is any surface configured for operatively coupling catheter tails 72, 74 (see FIG. 1) between the connector section 30 of the first connector 20 and the second connector 40. In one embodiment and by way of example and not by way of limitation, the catheter engaging body 31 engages an inner wall of a catheter lumen 64, 65 and/or portions of engaging surfaces 78, 79, 80, 81, 81', 84, 85, 86, 87, 86', and 88 (see FIGS. 10-12) of the tails 72, 74 of the proximal second end section of the catheter 60. The first connector lumen 21' extends through the proximal connector section 30 of the first connector 20 and through the catheter engaging body 31 of the first connector 20 such that the lumen 21' is in fluid communication with the distal insert lumen 21 (FIG. 3) to allow conveyance, regulation, flow, and/or movement of fluids, medication, and/or gases therethrough.

FIG. 2 also shows that, the catheter engaging body 31 may include an optional cylindrical portion 31'. In this alternative embodiment, the catheter tails 72, 74 (see FIG. 1) of the proximal second end section 63 of the catheter 60 may be disposed about the cylindrical portion 31' such that the catheter tails 72, 74 and optional cylindrical portion 31' are operatively coupled and form a connection (direct or indirect as with intervening parts) between the catheter tails 72, 74 and the optional cylindrical portion 31'. The term "disposed about," "dispose about," "disposes about," and variants thereof are not used lexicographically but instead are used herein to describe embodiments of the invention such that an item directly or indirectly (e.g., intervening parts) abuts, contacts, touches, and/or otherwise is positioned partially around (e.g., two or more catheter tails 72, 74 together are positioned substantially around) another item. The cylindrical portion 31' may be any suitable length. In one embodiment, it is approximately 0.080 inches in length, although it may be longer or shorter as desired.

Alternatively (or in addition to a cylindrical portion 31'), the catheter engaging body 31 may include an optional tapered engaging portion 31". In this alternative embodiment, the catheter tails 72, 74 may be disposed about the tapered engaging portion 31" so as to be operatively coupled and form a connection (direct or indirect as with intervening parts) between the catheter tails 72, 74 and the optional tapered engaging portion 31". By way of example only and not by way of limitation, the optional tapered engaging portion 31" engages an inner wall of a catheter lumen 64, 65 and/or portions of engaging surfaces 78, 79, 80, 81, 81', 84, 85, 86, 87, 86', and 88 (see FIGS. 10-12) of the tails 72, 74 of the proximal second end section of the catheter 60. The term "taper" in describing embodiments of the invention means that the tapered engaging portion 31" has an outer diameter that gradually becomes smaller, such as in a distal direction. For instance, a taper may be formed by altering the width, height, thickness, and/or cross sectional area of the tapered engaging portion 31" along the length of the catheter engaging body 31. The tapered engaging portion 31" may be any suitable length. In one embodiment, it is approximately 0.082 inches along the length of the catheter engaging body 31.

In one alternative embodiment of the invention illustrated in FIG. 2, the proximal connector section 30 also comprises an actuation body 32, the actuation body being configured for connecting (detachably or substantially fixedly) the first connector 20 and second connector 40. In this alternative embodiment, the first connector lumen 21' extends through the actuation body 32 and the catheter engaging body 31 of the proximal connector section 30 and is in fluid communication with the distal insert lumen 21 (FIG. 3) for allowing conveyance, regulation, flow, and/or movement of fluids, medication, and/or gases therethrough. The proximal connector section 30 includes at least one fastener 33 although it could have more than one fastener 33. Optionally, the actuation body 32 comprises the at least one fastener 33; alternatively, the catheter engaging body 31 may comprise the at least one fastener 33; or both the catheter engaging body 31 and the actuation body 32 may each comprise a fastener 33.

It should be understood that the at least one fastener 33 may be any structure for operatively coupling the first and second connecters 20, 40, respectively, so as to control or reduce the likelihood of undesired movement or separation of the connectors 20, 40. Optionally, the at least one fastener 33 comprises a clipping, clasping, clutching, holding, affixing, attaching, threading, connecting, coupling device, and/or other securing member. In one embodiment, the at least one fastener 33 comprises a male threaded outer surface of the first connector 20 for engaging a female thread of the second connector. For instance, the fastener 33 may comprise a thread that measures approximately thirty-two threads per inch and extends approximately 0.150 inches along the length of the actuation body 32, although the thread may be longer or shorter (along the length of the actuation body) as desired, and there may be more than one thread. If a one-time snap fit is desired, then the fastener 33 may be one or more circumferential ridges or barbs. In another embodiment where the luer assembly 10 may be put together as well as taken apart (e.g., for servicing, for replacing catheters), the fastener 33 may be one or more circumferential ridges in the form of knuckle threads (e.g., circumferential ridges forming complementary undulating waves). In yet another embodiment, the fastener 33 is an outer surface or outer diameter that friction fits, press fits, and/or wedges into engagement the fastener 33 of the first connector and a fastener 52 (FIGS. 5, 5A) of the second connector 40 to hold together (detachably or substantially fixedly) the first and second connectors. The operatively coupled first and second connecters 20, 40, respectively, according to these varying embodiments of fasteners 33 may be substantially fixed such that they do not rotate relative to each other, or may rotate while preventing undesired axial separation.

The actuation body 32 may further include an optional handle portion 34. By way of illustration and not by way of limitation, the handle portion 34 may be any prehensile member, a gripping surface, a grooved contour, grabbing object, assembly, and/or other structure that gives the physician control over the operation, actuation, handling, manipulation, and/or movement of the first connector 20. In one embodiment, the first connector lumen 21' extends at least partly through the optional handle portion 34 of the actuation body 32 and is in fluid communication with the distal insert lumen 21 (FIG. 3). In one embodiment, the handle portion 34 is approximately 0.172 inches in length and comprises a portion of the actuation body 32, although it may be longer or shorter as desired. The actuation body 32 may include an optional setoff 35 intermediate the handle portion 34 and the least one fastener 33. The optional setoff 35 is configured to ensure that the handle portion 34 may be easily controlled by the physician's hand or fingers without undue interference resulting from the female member 40. In one embodiment, the optional setoff 35 is approximately 0.060 inches in length and is formed integrally with a portion of the actuation body 32, although it may be longer or shorter as desired.

As shown in FIG. 2, the proximal connector section 30 may further comprise an optional syringe engaging hub 36 configured to operatively couple a syringe. In one embodiment, the syringe engaging hub 36 is proximal to the actuation body 32, although the syringe engaging hub 36 may be distal to or transverse to the actuation body 32. In an embodiment having an optional syringe engaging hub 36, the first connector lumen 21' extends through the optional syringe engaging hub 36, through the optional handle portion 34 of the actuation body 32, through the catheter engaging body 31, and is in fluid communication with the distal insert lumen 21 (FIG. 3) for allowing conveyance, regulation, flow, and/or movement of fluids, medication, and/or gases therethrough. The syringe engaging hub 36 may include a fastener 37 for operatively coupling the syringe and the syringe engaging hub 36. In one embodiment, the fastener 37 may comprise a thread, flange, protrusion, or rib for interlocking with a corresponding thread, flange, recess, or rib of a syringe (not shown). The optional fastener 37 may be approximately 0.050 inches along the length of the optional syringe engaging hub 36, although it may be longer or shorter as desired. The syringe engaging hub 36 may also have an optional setoff 39 intermediate the handle portion 34 and the syringe engaging hub 36. The optional setoff 39 is configured to ensure that the syringe (not shown) may be easily actuated, such as by the physician's hand or fingers, without undue interference resulting from the handle portion 34. In one embodiment, the optional setoff 39 is approximately 0.148 inches in length and comprises a portion of the optional syringe engaging hub 36, although it may be longer or shorter as desired.

FIG. 2A shows an alternative embodiment of the first connector 20. In this embodiment, the first connector distal insert 22 further comprises at least one insert fastener 28 at or near the first connector catheter engaging body 31 for securing (detachably or substantially fixedly) within the catheter lumen (64, 65) such as, by way of example only and not by way of limitation, a friction fit, press fit, and/or wedge. Proximally, the fastener 28 may abut the first connector catheter engaging body 31 or be positioned (entirely or partially) within one inch distally of a catheter engaging body aperture 29 (FIG. 3) discussed below. The at least one insert fastener 28 may be any structure for helping to secure the catheter second end section 63 and/or a distal portion of catheter tails 72, 74 (see FIG. 1). In one embodiment and by way of example and not by way of limitation, the at least one insert fastener 28 comprises a threaded outer surface for engaging an inner wall of a catheter lumen 64, 65 and/or portions of engaging surfaces 78, 79, 80, 81, 81', 84, 85, 86, 87, 86', and 88 (see FIGS. 10-12) of the tails 72, 74 of the proximal second end section 63 of the catheter 60.

FIG. 3 shows a longitudinal, sectional view of one embodiment of the first connector 20 taken along the lines 3-3 of FIG. 2 (together with other optional features described above) according to the luer assembly 10 embodiment of the invention and/or for use with a method of the present invention.

FIG. 3 further shows an opening 26 located at or near the distal first end 23 of the distal insert 22. Optionally, the first end opening 26 is in fluid communication with the exterior of the distal insert 22 (e.g., the volume external to the first end opening 26; directed toward a lumen 64, 65 of the catheter 60; and/or the space external the distal insert 22). FIG. 3 also shows that the insert 22 comprises an optional proximal second end 25, wherein the insert 22 comprises an opening 27 at or near the insert proximal second end 25. The openings 26, 27 define the distal insert lumen 21 that is in fluid communication with the lumen 21' of the connector section 30 for allowing conveyance, regulation, flow, and/or movement of fluids, medication, and/or gases therethrough.

The catheter engaging body 31 and distal insert 22 according to the invention may be formed integrally or, optionally, may be separate pieces that are operatively coupled by any suitable means. When they are operatively coupled, the catheter engaging body 31 and the distal insert 22 may be directly or indirectly-as through intervening parts-mechanically, chemically, and/or chemical-mechanically bonded, joined, adjoined, connected, associated, united, mated, interlocked, conjoined, fastened, held together, clamped, crimped, sandwiched, viced, engaged, friction fitted, press fitted, wedged, a joint, a junction, a juncture, a seam, a union, a socket, and/or held together by soldering, brazing, welding, glue, adhesives, resins, chemical bonding materials or combinations thereof and the like. If operatively coupled, the catheter engaging body 31 optionally comprises an aperture 29 (FIG. 3) for receiving the proximal second end 25 of the insert 22, and the insert proximal second end 25 extends approximately 0.162 inches within the lumen 21' of the proximal connector section 30 and proximal to the aperture 29.

FIG. 3 also shows the proximal connector section 30 with an optional syringe receptacle 38. The syringe receptacle 38 is configured for receiving a portion of a syringe (not shown) within the first connector 20. In one embodiment, the syringe receptacle 38 extends within the optional syringe engaging hub 36 and the optional handle portion 34 of the actuation body 32, although the syringe receptacle 38 may also extend within the catheter engaging body 31. The optional syringe receptacle 38 is in fluid communication with the lumens 21, 21' for allowing conveyance, regulation, flow, and/or movement of fluids, medication, and/or gases therethrough. Thus, the insert proximal first end opening 26 may be in fluid communication with the insert lumen 21, the first connector lumen 21', and the optional syringe receptacle 38. Alternatively, and in accordance with another aspect of the invention, the lumens 21, 21' and receptacle 38 can be separated by additional intervening spacings, passageways, or occlusions, bushings, diaphragm seals, and/or valves (and/or valve/diaphragm seal equivalents) configured to open/close and otherwise allow fluid communication from the first end opening 26 to the proximal connector section lumen 21' and/or the optional syringe receptacle 38 and distally in communication with the insert lumen 21.

FIG. 4 illustrates a perspective view of one embodiment of a second connector 40 according to the invention. A second connector 40 may be any device, tool, apparatus, or component configured for engaging (detachably or substantially fixedly) a first connector 20 (see FIGS. 1-3) and a catheter 60 (see FIG. 1) disposed about the first connector distal insert 22 and the tails 72, 74 of the catheter second end section 63 operatively coupled between the first and second connectors 20, 40, respectively. The second connector 40 comprises a distal first end 42 and a proximal second end 44. The distal first end 42 and proximal second end 44 include first and second end openings 46, 48, respectively, defining a passageway 50 sized to be capable of receiving the distal first end 23 of the first connector distal insert 22 and a catheter proximal second end section 63. Optionally, the passageway 50 is sized to form a sufficiently tight seal against the first connector distal insert 22 and catheter 60 disposed about the first connector distal insert 22 so as to prevent within a sufficient tolerance any fluids from leaking into the passageway 50. The second connector 40 may be substantially rigid and may be made of any suitable material (natural, synthetic, plastic, rubber, metal, or combination thereof). The second connector 40 may be any suitable length, and in one embodiment is approximately 0.766 inches in length, although it may be longer or shorter as desired. In one embodiment, the second connector 40 is a female luer fitting connector.

Optionally, the second connector 40 may have a gripping surface 49. The gripping surface 49 may be any structure, component, device, or apparatus such as a handle, grooved contour, prehensile member, and/or grabbing object that gives the physician control over the operation, actuation, handling, manipulation, and/or movement of the second connector 40. By way of example, the gripping surface 49 may help a physician to rotate the second connector 40 relative to the first connector 20 for operatively coupling the first and second connectors 20, 40, respectively. In one embodiment, the gripping surface 49 is an undulating grip that includes a series of longitudinal or transverse wave crests comprising troughs extending between the crests. The gripping surface 49 may extend approximately the entire longitudinally length of the second connector 40.

FIGS. 5 and 5A show longitudinal, sectional views of alternative embodiments of the second connector 40 according to FIG. 4 for use with the method of the present invention. FIG. 5 further shows a proximal cavity 51 at or near the second end 44 sized for receiving the catheter engaging body 31 of the first connector 20 and/or sized for receiving at least a portion of the at least one fastener 33 of the actuation body 32 of the first connector catheter section 30. In one embodiment, the passageway 50 defines, includes, or otherwise is in fluid communication with the proximal cavity 51 and thereby configured to accommodate (e.g., sized to contain or stretch to contain or receive or allow passage of) the first connector distal insert 22 through the second connector proximal second end opening 48 and external to the second connector distal first end opening 46. Alternatively, the cavity 51 and passageway 50 can be separated by additional intervening spacings, passageways, and/or occlusions, bushings, diaphragm seals, and/or valves (and/or valve/diaphragm seal equivalents) configured to open/close and otherwise allow fluid communication from proximal second end opening 48 to the distal first end opening 46.

FIG. 5 further shows at least one fastener 52 within the second end cavity 51 of the second connector 40. It is understood that the at least one fastener 52 may be any structure for helping, controlling, or preventing undesired movement or separation of the first and second connectors 20, 40, respectively. Optionally, the at least one fastener 52 comprises a clipping, clasping, clutching, holding, affixing, attaching, threading, connecting, coupling device, and/or other securing member. In one embodiment, the at least one fastener 52 comprises a female threaded inner surface of the second connector 40 for engaging a male threaded outer surface (e.g., a fastener 33) of the first connector such that the second connector fastener 52 operatively couples the first connector fastener 33. In one embodiment, the fastener 52 comprises a femal threaded inner surface having a thread that measures approximately thirty-two threads per inch and is approximately 0.150 inches along the length of the second end 44, although the thread may be longer or shorter (along the length of the second connector) as desired, and there may be more than one thread. If a one-time snap fit is desired, then the fasteners 33, 52 may be one or more circumferential ridges or barbs. In another embodiment where the luer assembly 10 may be put together as well as taken apart (e.g., for servicing, for replacing catheters), the fasteners 33, 52 may be one or more circumferential ridges in the form of knuckle threads (e.g., circumferential ridges forming complementary undulating waves). In yet another embodiment, the fastener 52 is an inner surface or inner diameter that friction fits, press fits, and/or wedges the fastener 33 of the first connector and a fastener 52 (FIGS. 5, 5A) of the second connector 40 to hold together (detachably or substantially fixedly) the first and second connectors. The operatively coupled first and second connecters 20, 40, respectively, according to these varying embodiments of fasteners 33, 52 may be substantially fixed such that they do not rotate relative to each other, or may rotate while preventing undesired axial separation.

As shown in FIG. 5, the second connector 40 further comprises a catheter engaging body 53 at or near the second end cavity 51. The catheter engaging body 53 may be any surface configured for disposing about the catheter tails 72, 74 (see FIG. 1) of the proximal second end section 63 of the catheter 60, which tails 72, 74 in one embodiment would be operatively coupled between the catheter engaging body 31 (and/or the optional cylindrical portion 31' and/or the optional tapered engaging portion 31") of the connector section 30 of the first connector 20 and the second connector catheter engaging body 53. Optionally, the catheter engaging body 53 may be cylindrical and substantially similar to but having a greater inner diameter than an outer diameter of the optional cylindrical portion 31' of the first connector 20. Alternatively or in addition to a cylindrical portion, the catheter engaging body 53 optionally is tapered and similar to the optional tapered engaging portion 31" of the first connector 20. In another embodiment, the second connector catheter engaging body 53 is sized to accommodate (e.g., sized to contain or stretch to contain or receive or allow passage of) a portion of the connector section 30 and catheter tails 72, 74 and proximal second end section 63 (see FIG. 1).

In FIG. 5A, the second connector 40 further has an insert fastener receiving cavity 54 configured to be placed over, receive, and/or operatively couple the insert fastener 28 (see FIG. 2A) of the first connector distal insert 22. Also, the cavity 54 is sized to be capable of accommodating (e.g., sized for containing or stretching to contain or receiving or allowing passage of) an assembly comprising the insert fastener 28 and catheter proximal second end section 63 (i.e., accommodating the fastener 28 and the catheter proximal second end section 63 that is at least partially disposed about the fastener 28) and/or the catheter tails 72, 74 of the catheter proximal second end section 63.

FIG. 6 is a schematic representation of a catheter 60 comprising a distal first end 61, an elongate (long) middle portion 62, and a proximal second end section 63. In describing an embodiment of the invention, the term "catheter" shall have its plain and ordinary meaning, rather than any lexicographic definition. Given the configuration of a vessel passageway or the channel of an endoscope or accessory device, a variety of catheters 60 of different shapes and sizes can be used depending on the particular medical procedures/applications intended for the catheter. For instance, an embodiment of a suitable catheter 60 comprises a tubular member, which may be better tolerated by the patient to minimize pain and discomfort during the medical procedure/application than other configurations. The term "tubular" in describing this embodiment includes any tube-like, cylindrical, elongated, shaft-like, rounded, oblong, or other elongated longitudinal shaft extending between a distal first end 61, an elongate (long) middle portion 62, and a proximal second end section 63. The catheter 60 may be straight or may at times even be curved, because as explained below, any one or more of the distal first end 61, middle portion 62, and/or proximal second end section 63 may be flexible.

Similarly, the dimensions of the catheter 60 will depend on various factors. These factors include the intended use of the catheter 60 and the vessel passageway or the channel of an endoscope or accessory device into which the catheter will be positioned. In general, however, the catheter middle portion 62 is elongate, meaning that it is sized relatively long enough to reach a target site at a region internal the patient's body. The overall catheter length may vary greatly, however, depending on the intended medical procedure for the device and the location of the target site internal the patient's body. In one embodiment, the length of the catheter 60 and/or elongate middle portion 62 may be in the range of between about 50 centimeters ("cm") and about 600 cm, although the length of the catheter and/or middle portion may be shorter or longer as desired. Alternatively, these lengths may range from about 100 cm to about 480 cm. For a catheter intended to be used in a common bile duct, one example of a suitable length may be in the range from approximately 175 to approximately 225 cm.

Just as the catheter length may vary, so, too, the catheter outer diameter also may vary along the length of the catheter. In one embodiment, the catheter may have a substantially constant outer diameter. In one embodiment, by way of illustration only, an outer diameter may be in the range from between about 0.5 millimeters ("mm") and about 5.0 mm (although the diameter may be lesser or greater than this range). Optionally, the catheter may taper along a portion of its length such that a cross sectional area, outer diameter, and/or thickness at or near the distal first end 61 is smaller than a cross sectional area, outer diameter, and/or thickness at or near the proximal second end section 63 and/or the elongate middle portion 62. In another embodiment, the catheter 60 is substantially uniform from the proximal second end section 63 to the elongate middle portion 62 and to the distal first end 61.

In one embodiment, the catheter 60 has a length from approximately 25.0 inches to approximately 100.0 inches in length, although it may be longer or shorter as desired. In one embodiment, the middle portion 62 has a length of about 78.0 inches, the distal first end 61 has a length of about 2.0 inches, and the proximal second end section 63 has a length of about 2.0 inches, for an overall catheter 60 length of approximately 82.0 inches. In one embodiment, the catheter 60 tapers in the distal direction such that, by way of example, a cross sectional area, width, height, and/or thickness at the catheter distal end 61 is less than a cross sectional area, width, height, and/or thickness at the catheter proximal second end section 63.

The catheter middle portion 62 is substantially flexible. Optionally, the distal first end 61 and proximal second end section 63 are flexible, too, but in one embodiment the proximal second end section 63 may exhibit less flexibility or may even be rigid or semi-rigid relative to the middle portion 62 and/or the distal first end 61. Indeed, flexibility at the middle portion 62 and/or distal first end 61 helps the catheter to be inserted into a patient's vessel passageway or into a channel of an endoscope or an endoscope accessory device to be inserted into the patient's vessel passageway. Moreover, some flexibility helps the middle portion 62 and/or the distal first end 61 to navigate through bends and turns of the vessel passageway, the endoscope working channel, or the endoscope accessory channel.

A catheter 60 may be purchased from a vendor such as Zeus, Inc. in Orangeburg, S.C., from Cook Incorporated in Bloomington, Ind., from Cook Endoscopy in Winston-Salem, N.C., or, in the alternative, made by any methods of extrusion, pultrusion, injection molding, transfer molding, flow encapsulation, fiber winding on a mandrel, or lay-up with vacuum bagging, to name a few. A variety of suitable materials (natural, synthetic, plastic, rubber, metal, or combination thereof) may be used, so long as the middle portion 62 and the optionally flexible distal and/or proximal ends 61, 63, respectively, comprise materials that allow desired flexibility. For example, suitable materials include surgical stainless steel or biologically compatible metals, polymers, plastics, alloys (including super-elastic alloys), or composite materials that are either biocompatible or capable of being made biocompatible. By way of further illustration and not by way of limitation, suitable elastomeric materials may comprise a latex, silicone, urethane, thermoplastic elastomer, nickel titanium alloy, polyether ether-ketone ("PEEK"), polyimide, polyurethane, cellulose acetate, cellulose nitrate, silicone, polyethylene terephthalate ("PET"), polyamide, polyester, polyorthoester, polyanhydride, polyether sulfone, polycarbonate, polypropylene, high molecular weight polyethylene, polytetrafluoroethylene ("PTFE"), or mixtures or copolymers thereof, polylactic acid, polyglycolic acid or copolymers thereof, polycaprolactone, polyhydroxyalkanoate, polyhydroxy-butyrate valerate, polyhydroxy-butyrate valerate, or another polymer or suitable material.

FIG. 6 also shows that the catheter 60 further comprises at least a first lumen 64 and a second lumen 65. The first lumen 64 has a proximal opening 66 at the proximal second end section 63 and a distal opening 56 at or near the catheter distal first end 61. The second lumen 65 has a proximal opening 67 at the proximal second end section 63 and a distal opening 57 at or near the distal first end 61. Optionally, the first and second lumens 64, 65, respectively, extend the entire length of the catheter 60 from their proximal openings 66, 67, respectively, to their distal openings 56, 57, respectively, at or near the distal first end 61. Alternatively, the lumens 64, 65 do not extend all the way to the most distal tip of the catheter distal first end 61, such as when distal lumen openings 56, 57, respectively, extend to and are in fluid communication with the exterior (e.g., the volume external to the openings) of the outer sidewall of the catheter distal first end 61 or the outer sidewall of the catheter elongate middle portion 62 at or near the catheter distal first end 61. The first lumen 64 and second lumen 65 at the catheter proximal second end section 63 are sized to be capable of accommodating (e.g., sized to contain or stretching to contain or receiving or allowing passage of) a first connector distal insert 22 (see FIGS. 1-3). The first and second lumens 64, 65, respectively, are configured for allowing conveyance, regulation, flow, and/or movement of fluids, medication, and/or gases.

The proximal first lumen opening 66 and proximal second lumen opening 67 are radially offset relative to the proximal end central longitudinal axis 68 (e.g., their respective lumen openings 66 and 67 are not co-axial with the central longitudinal axis 68). In one embodiment, at least one of the first and second lumens 64, 65, respectively, at the proximal second end section 63 prior to slitting 70 are substantially parallel to the central longitudinal axis 68. In another embodiment, the first lumen 64 and second lumen 65 at the proximal second end section 63 are substantially parallel to each other. Optionally, there are more than two lumens offset relative to the proximal end central longitudinal axis 68.

For clarity, the proximal end central longitudinal axis 68 is shown as an oversized dot with cross hatchings in FIGS. 7-9, but it should be understood that the central longitudinal axis 68 may but need not have any area (or volume) to it. The central longitudinal axis 68 is the longitudinal lengthwise axis of the catheter proximal second end section 63, which may be straight or may at times even be curved if the proximal second end section 63 is flexible. Furthermore, the central longitudinal axis 68 is substantially central to the extent that it need not be central to a mathematical certainty-just approximately central.

In one embodiment, the proximal first lumen 64 at the proximal first lumen opening 66 has a greater inner diameter relative to the smaller inner diameter of the proximal second lumen 65 at the proximal second lumen opening 67. In one embodiment and by way of illustration and not by way of limitation, the catheter proximal second end section 63 is approximately 0.0715 inches in outer diameter, the second lumen 65 at the opening 67 has an inner diameter that is approximately 0.020 inches, and the first lumen 64 at the opening 66 has an inner diameter that is approximately 0.040 inches.

FIGS. 7, 8, and 9 are alternative schematic end views of an end face 69 of a proximal second end section 63 of a catheter 60. These figures show alternative embodiments of slitting 70 the proximal second end section 63 across the end face 69 of catheter 60 for use with the luer assembly 10 or the method of the present invention. The end face 69 is the proximal surface of the proximal second end section 63 viewed end-on in the distal direction. In one embodiment, the end face 69 is approximately planar geometry with at least one of the lumens 64, 65 therethrough. In another embodiment, the end face 69 may be non-planar, round, contoured, or having one or more curves or other surface that defines the end-on view in the distal direction of the catheter proximal second end section 63. In one embodiment, the catheter proximal second end section 63 and/or end face 69 have an outer diameter that is approximately 0.0715 inches in width.

FIGS. 7, 8, and 9 show a slit 70 across an end face 69 of the proximal second end section 63. The slit 70 may intersect one or both of the first and second lumens 64, 65, respectively, and their corresponding openings 66, 67, respectively. Although FIGS. 7, 8, and 9 show a two-lumen catheter, an alternative embodiment of the invention may comprise a single-lumen catheter where the slit 70 intersects, for example, the lumen 64, which lumen 64 and corresponding opening 66 may be substantially co-axial with the proximal end central longitudinal axis 68. Also, FIGS. 7, 8, and 9 may illustrate a catheter having more than two lumens. For conciseness, however, only a two-lumen embodiment will be described, but in an embodiment with three or more lumens the slit 70 may cross one or a combination of the lumens. The term "slit" 70 and "slitting" 70 and variants thereof are used not as a lexicographic definition but to describe embodiments of the invention having any lengthwise cut or notch across at least a portion of the end face 69 at the catheter distal end 63 and being coaxial, parallel, angled, or offset relative to the proximal end central longitudinal axis 68.

The slit 70 may be a cut or notch across one or more of the lumens. In FIG. 7, for instance, the slit 70 crosses the first lumen 64 and its opening 66, the second lumen 65 and its opening 67, and is coaxial with the proximal end central longitudinal axis 68. In FIG. 8, the slit 70 crosses the first lumen 64 and its opening 66, and is parallel to and offset from the proximal end central longitudinal axis 68. In FIG. 9, the slit 70 crosses the first lumen 64 and its opening 66, and is radially offset from the proximal end central longitudinal axis 68 and optionally angled relative to the proximal end central longitudinal axis 68 such that if the slit 70 were deep enough in the lengthwise direction it may optionally intersect the proximal end central longitudinal axis 68.

The slit 70 may cut or notch the catheter proximal second end section 63 into two equal or unequal parts and/or portions labeled as tails 72, 74 (see FIGS. 10, 11, and 12). In one embodiment for example, the slit 70 intersects and is coaxial with the catheter proximal end central longitudinal axis 68 so as to bisect the lumens 64, 65 and opening 66, 67 and result in approximately equal tails 72, 74 (see FIG. 7). In another embodiment, the slit 70 is offset relative to the catheter proximal end central longitudinal axis 68 so as to intersect a lumen 64, 65 and an opening 66, 67 and thereby cleaving the catheter proximal second end section 63 into unequally dimensioned (e.g., thicknesses, perimeters) tails 72, 74 and/or two unequal portions (see FIGS. 8 and 9). In addition, two or more slits 70 across the end face 69 may cut or notch the catheter proximal second end section 63 so as to slice the catheter proximal second end section 63 into 3, 4, or more equal or unequal parts or portions in thicknesses, perimeters, and the like, such as by way of example only and not by way of limitation, if the slit 70 from FIG. 7 were combined with a second slit that is rotated, for instance, 90 degrees about the end face 69 so that the pair of slits 70 form right angles in an "X-shaped" configuration. Slits need not cross the entire diameter of the end face 69, as when three radial slits 70 intersect to divide the catheter proximal second end section 63 into, by way of example only and not by way of limitation, three equally shaped tails (e.g., wherein the radial slits intersect at 120 degree angles), two equally shaped tail and one unequal tail (e.g., such as a "Y-shaped" configuration); or all unequally shaped tails (e.g., such as a "T-shaped" configuration).

FIG. 10 is a perspective view of the catheter 60 of FIG. 7 and showing an embodiment of a slit 70 at the catheter proximal second end section 63. The first tail 72 and the second tail 74 are approximately symmetrical. The first tail 72 has a first inner engaging surface 78 and a second inner engaging surface 80 to dispose about the catheter engaging body 31 of the first connector 20. The first tail 72 further includes an outer engaging surface 82 to dispose about the catheter engaging body 53 of the second connector 40. Similarly, the second tail 74 has a first inner engaging surface 84 and a second inner engaging surface 86 to dispose about the catheter engaging body 31 of the first connector 20. The second tail 74 further includes an outer engaging surface 88 to dispose about the catheter engaging body 53 of the second connector 40. When the slit 70 crosses both lumens as in the embodiment shown in FIG. 10, then the first tail 72 also may comprise an interstitial engaging surface 79 and peripheral engaging surfaces 81, while the second tail 74 also may comprise an interstitial engaging surface 85 and peripheral engaging surfaces 87 to dispose about the catheter engaging body 31 of the first connector 20.

It should be understood that, when the first connector 20 and second connector 40 are operatively coupled, it is not required that all engaging surfaces described above or below as disposing about the catheter engaging body 31 of the first connector 20 or catheter engaging body 53 of the second connector 40 must contact those engaging bodies 31, 53. Rather, fewer than all of the engaging surfaces may contact (dispose about) the engaging bodies 31, 53. Furthermore, when an engaging surface does (dispose about) the catheter engaging body 31 of the first connector 20 or catheter engaging body 53 of the second connector 40, less than all of that engaging surface needs to contact those engaging bodies 31, 53. Rather, there need only be sufficient contact between that engaging surface and those engaging bodies 31, 53 so that the tails 72, 74 and/or the catheter proximal second end section 63 do not pull out from between the first and second connectors 20, 40, respectively. In one embodiment, the operatively coupling provides a pull out strength of at least 5 newtons and preferably a pull out strength of at least 20 newtons. In other words, as the tails 72, 74 are squeezed between the catheter engaging bodies 31, 53, the engaging surfaces need not form a circumference about those catheter engaging bodies 31, 53 of the first and second connectors 20, 40, respectively. Thus, some engaging surfaces will have more contact compared to other engaging surfaces with the engaging bodies 31, 53, and the tails would still exhibit sufficient holding power operatively coupled between the first and second connector catheter engaging bodies 31, 53.

FIG. 11 is a perspective view of the catheter 60 of FIG. 8 showing an alternative embodiment of a slit 70 at the catheter proximal second end section 63. The first tail 72 has an inner engaging surface 78 and peripheral engaging surfaces 81 to dispose about the catheter engaging body 31 of the first connector 20. The first tail 72 further includes an outer engaging surface 82 to dispose about the catheter engaging body 53 of the second connector 40. The second tail 74 has an inner engaging surface 84 and peripheral engaging surfaces 87 to dispose about the catheter engaging body 31 of the first connector 20. Similarly, the second tail 74 further includes an outer engaging surface 88 to dispose about the catheter engaging body 53 of the second connector 40. The first tail 72 and the second tail 74 are asymmetrical in cross sectional surface area (e.g., thicknesses and/or outer perimeters). The first tail engaging surfaces 78, 81 and the second tail engaging surfaces 84, 87 are approximately equal in surface area for disposing about the catheter engaging body 31 of the first connector 20. In contrast, the first tail outer engaging surface 82 has less surface area than the second tail outer engaging surface 88 for disposing about the catheter engaging body 53 of the second connector 40. In an alternative embodiment, the slit 70 may cut across the opening 67 of the smaller second end lumen 65 (e.g., the opening 67 of the lumen 65 represented in FIG. 8) of the catheter proximal second end section 63 (as opposed to cutting the opening 66 of the first lumen 64 shown in FIG. 11), such that in this alternative embodiment of FIG. 11 the second tail outer engaging surface 88 has greater surface area than the first tail outer engaging surface 82.

FIG. 12 is a perspective view of the catheter 60 of FIG. 9 showing an alternative embodiment of a slit 70 at the catheter proximal second end section 63. The first tail 72 has an inner engaging surface 78, a first peripheral engaging surface 81, and a second peripheral engaging surface 81' to dispose about the catheter engaging body 31 of the first connector 20. The second peripheral engaging surface 81' has less surface area than the first peripheral engaging surface 81 for disposing about the catheter engaging body 31 of the first connector 20. The first tail 72 further includes an outer engaging surface 82 to dispose about the catheter engaging body 53 of the second connector 40. Similarly, the second tail 74 has an inner engaging surface 84, a first peripheral engaging surface 87, and a second peripheral engaging surface 87' to dispose about the catheter engaging body 31 of the first connector 20. The second peripheral engaging surface 87' has less surface area than the first peripheral engaging surface 87 for disposing about the catheter engaging body 31 of the first connector 20. The second tail 74 further includes an outer engaging surface 88 to dispose about the catheter engaging body 53 of the second connector 40. The first tail 72 and the second tail 74 are roughly symmetrical in cross sectional surface area (e.g., thicknesses and/or perimeters). The first tail engaging surfaces 78, 81 and the second tail engaging surfaces 84, 87 are approximately equal in surface area for disposing about the catheter engaging body 31 of the first connector 20. In contrast, the first tail outer engaging surface 82 has less surface area than the second tail outer engaging surface 88 for disposing about the catheter engaging body 53 of the second connector 40.

While FIGS. 10, 11, and 12 show two tails 72, 74, there may be additional tails. As taught above, there may be more than one slit 70 such that there are three or more tails for disposing about the first connector catheter engaging body 31 and the second connector catheter engaging body 53. Thus, there may be additional engaging surfaces having lesser or greater surface area than the engaging surfaces 78, 81, 82, 84, 87, and 88.

The slit 70 as illustrated in FIGS. 10, 11, and 12 has a longitudinal slit length 76, which slit length 76 may vary. The longitudinal slit length 76 is measured along the length of the catheter second end section 63 and/or catheter proximal end central longitudinal axis 68 of the catheter second end section 63 of the catheter 60, and the slit 70 may be parallel to or angled relative to (e.g., intersecting) the central longitudinal axis 68. The length of the tails 72, 74 corresponds approximately to the slit length 76 if the slit 70 is parallel to the central longitudinal axis 68 or substantially corresponding to the slit length 76 or angled relative to the central longitudinal axis 68. In one embodiment, the slit length 76 (and, therefore, the approximate length of the tails 72, 74) is from about 2.0 mm to about 5.0 mm in length. If a slit length 76 is much deeper cut than approximately 5.0 mm is made, then the first and second tails 72, 74, respectively, may extend too far proximal to the first connector catheter engaging body 31 and second connector catheter engaging body 53, and thereby may dispose about and/or otherwise interfere with the first connector fastener 33 and the second connector fastener 52 such that the fasteners 33, 52 do not optimally operatively couple the first connector 20 and second connector 40. If a slit length 76 is too much shorter than about 2.0 mm, then the first and second tails 72, 74, respectively, may not dispose about enough of the first connector catheter engaging body 31 and the second connector catheter engaging body 53 to form a joint with sufficient holding power when the first connector 20 and second connector 40 are operatively coupled.

Figure 13:
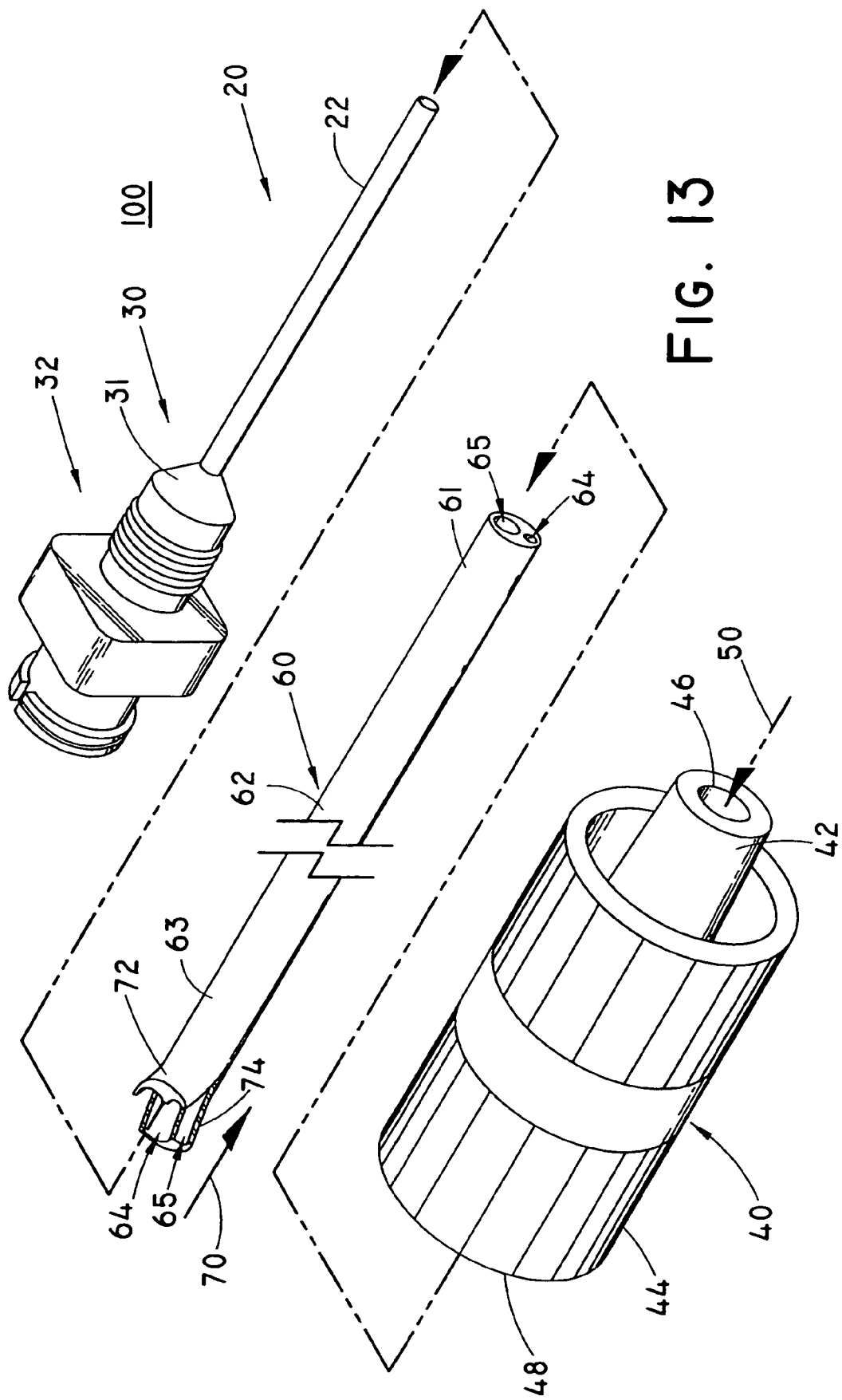
FIG. 13 is a schematic diagram illustrating a method of operatively coupling a first connector, a second connector, and a catheter according to one embodiment of the present invention.

FIG. 13 is a schematic diagram illustrating a method 100 of operatively coupling a first connector 20 as taught above, a second connector 40 as taught above, and a catheter 60. As shown, the first connector 20 has a catheter engaging body 31, wherein the catheter engaging body 31 optionally is part of a connector section 30 that further comprises an optional actuation body 32 as described above. The second connector 40 comprises a distal first end 42 with an opening 46 and a proximal second end 44 with an opening 48, the openings defining a passageway 50 sized to be capable of accommodating (e.g., sized to contain or stretching to contain or receiving or allowing passage of) the first connector distal insert 22 and the catheter.

The catheter 60 has at least a first lumen 64, and optionally a second lumen 65, although as previously explained the connector 60 could have one, two, or more lumens. For brevity, only a two-lumen catheter will be described. The catheter 60 comprises a distal end 61, an elongate (long) middle portion 62, a proximal second end section 63, and the first lumen 64 (and the optional second lumen 65) extending from the proximal second end section 63 to or near the distal end 61. The proximal second end section 63 further comprises a slit 70 forming a first tail 72 and a second tail 74, the slit 70 exposing at least one of the lumens 64, 65.

The first connector distal insert 22 is inserted into the first or second lumens 64, 65, respectively, of the catheter, and the first and second connectors 20, 40, respectively, and first and second tails 72, 74 of the proximal second end section 63 are operatively coupled as described above. The method 100 comprises steps that will not be described as shown schematically in FIGS. 13, 13A, 13B, 13C, and 13D according to one embodiment of the invention.

FIG. 13A shows two steps of the method 100 according to FIG. 13A. The first connector 20 is provided (step 110). Also, the catheter 60 is provided (step 120).

FIG. 13B illustrates other steps of the method 100 according to FIG. 13. The second connector 40 is provided (step 130) as described above to have a proximal second end section 63 comprising tails 72, 74. The first connector distal insert 22 is inserted (step 140) into one of the lumens exposed by the slit 70 such that the catheter tails 72, 74 dispose about the first connector catheter engaging body 31 (see FIG. 13B). As shown in FIG. 13B for illustrative purposes, the first connector distal insert 22 is inserted (step 140) into the catheter first lumen 64. The second connector 40 is moved (step 160) over the first connector catheter engaging body 31, such that the second connector catheter engaging body 53 may (e.g., is in a position to) operatively couple the catheter tails 72, 74 between the first connector catheter engaging body 31 and the second connector catheter engaging body 53—including for example any position whereby the fasteners 33, 52 may operatively couple and/or the first and second connectors 20, 40, respectively, may operatively couple and/or the engaging bodies 31, 53 may squeeze (directly or indirectly) the catheter tails 72, 74 and/or catheter proximal second end section 63 therebetween as previously described. In one embodiment of the moving step (step 160) by way of example and not by way of limitation, the second connector 40 may be moved (step 160) into position by inserting the catheter distal end 61 into the second connector proximal second end opening 48, within the second connector passageway 50, out the second connector distal first end opening 46, and then sliding the second connector 40 proximally over the catheter middle portion 62, the catheter tails 72, 74, and at least a portion (e.g., a catheter engagement body 31 and/or an actuation body fastener 33) of a connector section 30 of the first connector 20.

In one embodiment, the inserting step (step 140) further comprises a first connector 20 comprises a distal insert 22 having a distal first end 23 and a proximal second end 25, the distal first end 23 being inserted into the catheter lumen 64, 65. Optionally, the insert proximal second end 25 comprises a fastener 28 and the inserting step (step 140) comprises inserting the distal first end 23 within the catheter lumen 64, 65 such that the insert proximal second end fastener 28 engages the catheter proximal second end section 63 wherein the term engages includes directly or indirectly—as through intervening parts—detachably or substantially fixedly securing, joining, adjoining, connecting, associating, uniting, mating, interlocking, conjoining, fastening, holding together, clamping, crimping, sandwiching, engaging, friction fitting, press fitting, and/or wedging directly or indirectly the insert proximal second end fastener 28 and the catheter proximal second end section 63.

FIG. 13C further shows a sectional view of the catheter tails 72, 74 the proximal second end section 63 of the catheter, wherein the catheter tails 72, 74 are being disposed about (step 150) the first connector catheter engaging body 31. For illustrative purposes, the tails 72, 74 are shown slightly spaced from the first connector catheter engaging body 31. In practice, the tails 72, 74 may directly or indirectly (e.g., intervening parts) mostly abut, contact, touch, and/or otherwise be positioned partially around (and two or more catheter tails 72, 74 may be positioned substantially around) the first connector catheter engaging body 31. In describing an embodiment, the term "mostly" leaves open the possibility that, due to the contours of the tails and their engaging surfaces described in connection with and shown in FIGS. 10-12, there may be some space and gaps given any potential uneven contacting surface(s) formed by and/or between certain engaging surfaces 78, 79, 80, 81, 81', 84, 85, 86, 87, 86', and 88 configured for disposing about (step 150) the first connector catheter engaging body 31.

As shown in FIG. 13C, the first connector fastener 33 and second connector fastener 52 are operatively coupled (step 155) such that the catheter tails 72, 74 are operatively coupled between the first connector catheter engaging body 31 and the second connector catheter engaging body 53. Indeed, as explained above, the second connector 40 has at least one fastener 52 configured to operatively couple with at least one first connector fastener 33. In an embodiment where a one-time snap fit is desired for the first and second connectors, then the fasteners 33, 52 may be one or more circumferential ridges or barbs that operatively couple (step 155). In another embodiment, the fasteners 33, 52 could be knuckle threads (e.g., circumferential ridges forming complementary undulating waves) that operatively couple (step 155) by snapping the connectors together so that the luer assembly 10 may be put together as well as taken apart (e.g., for servicing, for replacing catheters). In yet another embodiment, the fasteners 33, 52 may be operatively coupled (step 155) by a friction fit, press fit, and/or wedge to hold together (detachably or substantially fixedly) the first and second connectors. Therefore, the first connector fastener 33 and second connector fastener 52 may be operatively coupled (step 155) such that the operatively coupled first and second connecters 20, 40, respectively, according to these varying embodiments of fasteners 33, 52 may be fixed such that the connectors 20, 40 do not rotate relative to each other or alternatively may rotate while preventing undesired axial separation. In one embodiment, the operatively coupling (step 155) provides a pull apart strength between the fasteners of at least 5 newtons and preferably a pull apart strength of at least 20 newtons.

As shown in FIG. 13E, if the fasteners 33, 52 of one embodiment according to FIG. 13D are male and female threads, then by way of example and not by way of limitation, the first connector 20 and second connector 40 may be operatively coupled by rotating (step 170) the second connector 40 relative to the first connector 20. The catheter tails 72, 74 are thereby secured between the first connector catheter engaging body 31 and the second connector catheter engaging body 53 as shown in FIG. 1. In one embodiment, the operatively coupling by rotating (step 170) provides a pull apart strength of at least 5 newtons and preferably a pull apart strength of at least 20 newtons.

The method 100 of operatively coupling a first connector 20, a second connector 40, and a catheter 60 according to the present invention need not be performed sequentially. For instance, the second connector 40 may be provided (step 130) before the first connector 20 is provided (step 110) and/or the catheter 60 is provided (step 120). Likewise, the catheter 60 may be provided (step 120) before the first connector 20 is provided (step 110) and/or the second connector 40 is provided (step 130). Furthermore, the second connector 40 may be moved (step 160) into position by inserting the catheter distal end 61 into the second connector proximal second end opening 48, and then the first connector distal insert 22 is inserted (step 140) into one of the lumens exposed by the slit 70 such that the catheter tails 72, 74 dispose about the first connector catheter engaging body 31. These are only examples to illustrate how the steps need not be performed sequentially.

Figures 14, 15:
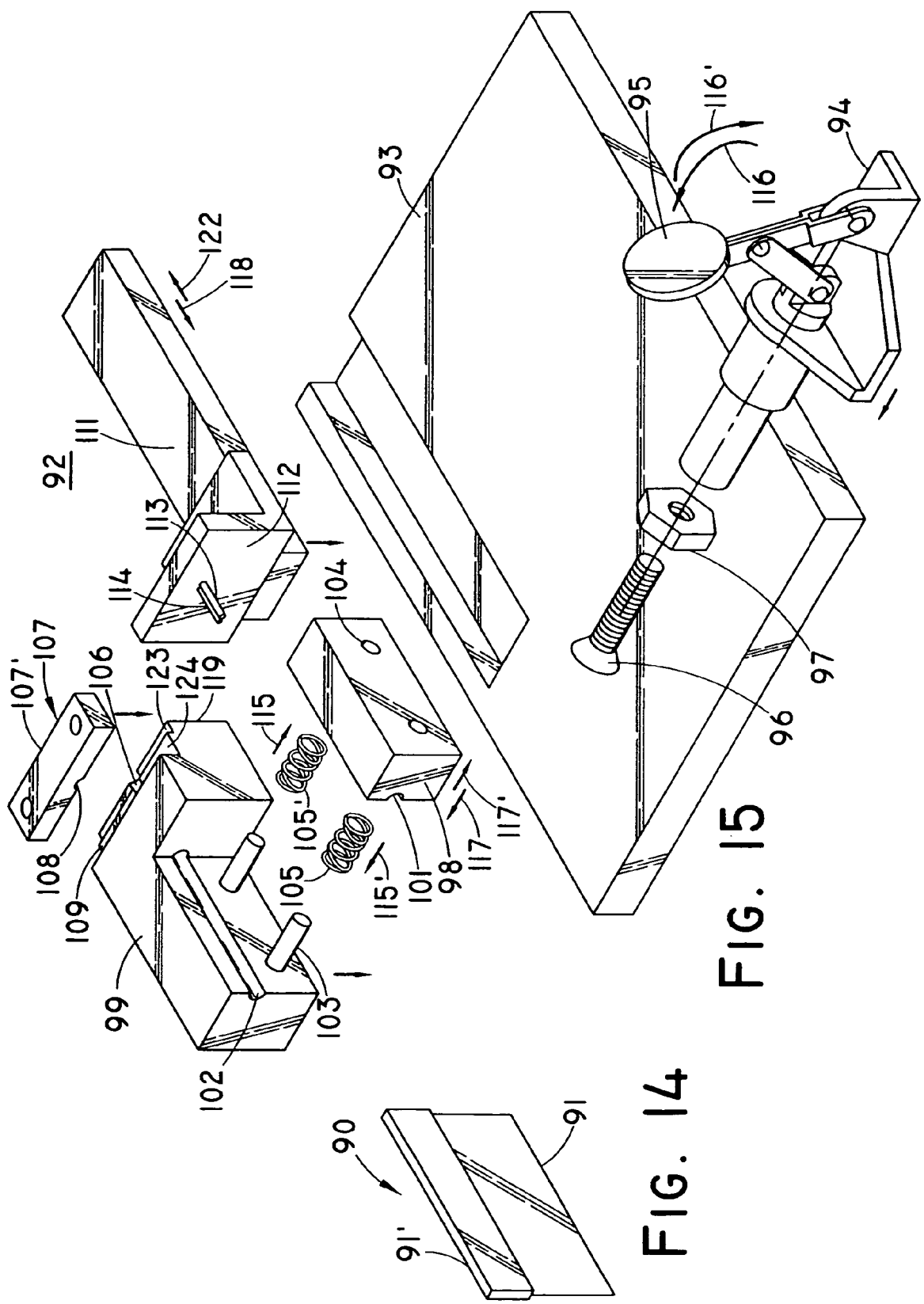
FIG. 14 shows a cutting tool according to the present invention.
FIG. 15 is an exploded view of a jig for slitting a catheter according to one embodiment of the present invention.

As shown in FIGS. 14 through 16E, a method 200 of cutting a catheter 60 at the proximal second end section 63 to form catheter tails 72, 74 is also provided. FIG. 14 shows one embodiment of a cutting tool 90 according to the present invention that is provided (step 210) in FIG. 16D. The cutting tool 90 may be any device having a cutting edge 91 (FIG. 14) configured for forming a slit 70. By way of illustration and not by way of limitation, the cutting edge 91 may be a razor blade, knife, or scalpel, or a thin wire heated or not heated with energy such as radiofrequency energy, or a laser. Optionally, the cutting tool 90 has a handle portion 91' for the user to hold during a cutting step. (FIG. 14).

Figure 16:
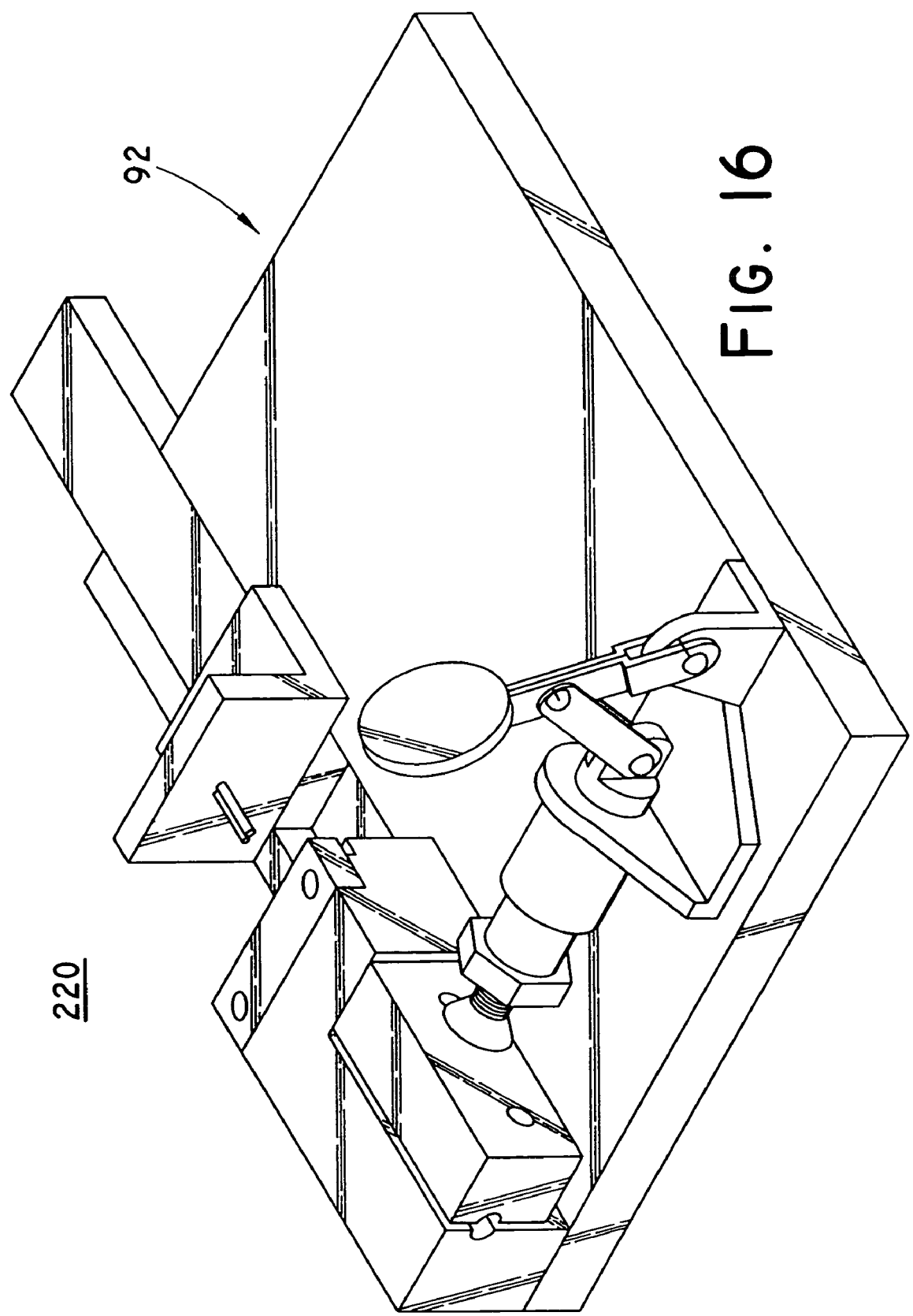
FIG. 16 is an assembled view of the jig shown in FIG. 15 according to one embodiment of the present invention.

FIG. 15 is an exploded view of a jig 92 that is provided (step 220) according to FIG. 16 (the assembled view of the jig 92 shown in FIG. 15 but, for clarity, without reference numerals of FIG. 15). The jig 92 is any suitable catheter locking member configured to secure a catheter proximal second end section 63 for slitting, such as by detachably securing the catheter between a catheter first guide 98 and a catheter second guide 99. Therefore, the jig 92 may be an operator's fingers or any tool, apparatus, device, and/or machine configured for holding a catheter proximal second end section 63 in place during a cutting step. One illustrative embodiment of the jig 92 will now be described.

FIG. 15 shows a perspective exploded view of one embodiment of a jig 92, for illustration and not by way of limitation, having a base plate 93, a clamp 94 secured to the base plate 93, the clamp 94 having a movable lever 95 for moving a screw 96 attached to the clamp by a nut 97. Also secured to the base plate 93 is a catheter first guide 98 that is moveable (e.g., slideable, not fixed) and a catheter second guide 99 that is stationary or capable of being made to be stationary (e.g., substantially fixed in position during clamping) for clamping a catheter proximal second end section 63 (e.g., FIG. 16A, see also FIG. 6) having been slideably placed between a catheter first guide groove 101 and a catheter second guide groove 102.

In one embodiment of a jig 92 shown in FIG. 15, the catheter second guide 99 has at least one optional guiding pin 103 inserted into an optional catheter first guide aperture 104 for providing proper alignment between the catheter first and second guides 98, 99 respectively, during a joining and clamping steps. An optional compression spring 105 disposes over the at least one guiding pin 103 between the catheter first and second guides 98, 99 respectively. The spring 105 optionally is sized larger in diameter than the catheter first guide aperture 104 and for returning the catheter first guide 98 into an unclamped position, or in another embodiment is sized to be received in the catheter first guide aperture 104 and is a sufficient length to extend out the aperture 104 for returning the catheter first guide 98 into an unclamped position.

In one embodiment, the catheter second guide 99 has an optional distal catheter groove 106 in fluid communication with the grooves 101, 102. The jig 92 also may comprise a spacer plate 107 having a catheter groove 108 corresponding to catheter second guide distal catheter groove 106 for receiving a catheter proximal second end section 63 for slitting. Optionally, the spacer plate 107 provides a slot 123 between the spacer plate 107 and a catheter second guide step 124 at or near an optional catheter guide distal slide face 119, the slot 123 corresponding with the depth for the slit 70 (not shown). Optionally, the spacer plate 107 is positioned distal to a slit stop 109 of the second catheter guide 99 and having an optional spacer plate distal slide face 107' flush with a distal slide face 119 of the catheter second guide 99. The jig 92 further may comprise a slide plate 111 moveable toward the catheter second guide 99, the slide plate 111 comprising a proximal face plate 112, and secured to the face plate 112 is a catheter first lumen alignment pin 113 and optionally a catheter second lumen alignment pin 114. Other steps and features of the jig 92 that are best shown in exploded view (FIG. 15) but discussed in context of other later figures include the following: the catheter first guide 98 and catheter second guide 99 are joined (step 115) and un-joined (step 115') sufficient to hold the catheter proximal second end section 63 therebetween; the first and second guides 98, 99 may further be clamped together (step 117) when the lever 95 is actuated (step 116) sufficient to ensure that the catheter proximal second end section 63 does not pull out or shift unintentionally, and unclamped (step 117') when the lever 95 is de-actuated (step 116'); and the catheter proximal second end section 63 is positioned (step 118) for cutting such as by a positioning member such as (by way of example only) a slide plate 111, and the positioning member (e.g., the slide plate 111) is withdrawn (step 122) to allow room for the cutting tool 90. In one embodiment, the operatively coupling provides a pull out strength of at least 5 newtons and preferably a pull out strength of at least 20 newtons.

Figure 16A:
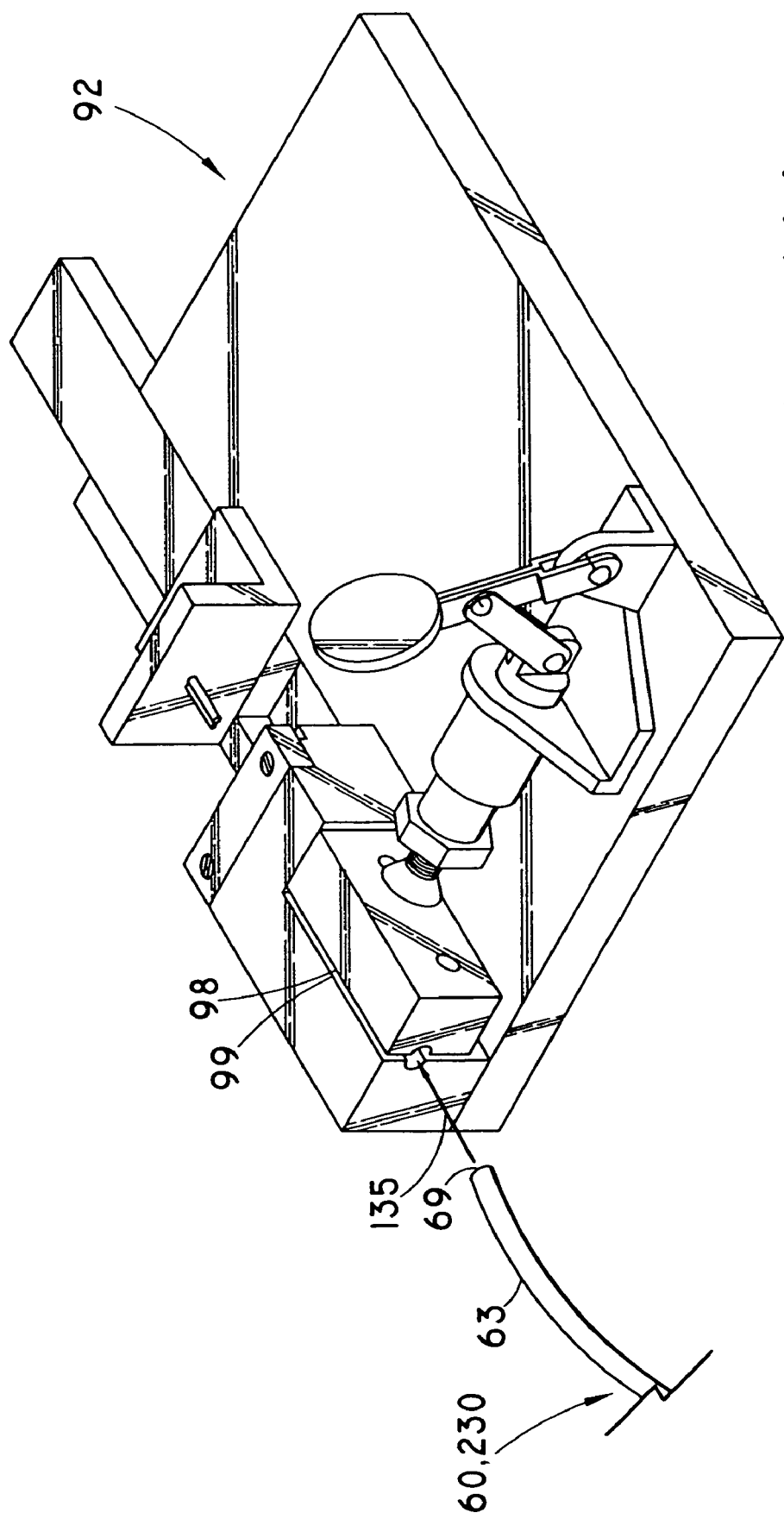
FIG. 16A illustrates a schematic diagram of a catheter being provided according to one embodiment of the present invention.

FIG. 16A shows a catheter 60 being provided (step 230). As described above (e.g., FIGS. 6), the catheter comprises a distal end 61, an elongate (long) middle portion 62, and a proximal second end section 63 having an end face 69. As previously described, the catheter 60 further comprises at least a first lumen 64 having an opening 66 at the catheter proximal second end section 63 and an opening 56 at or near the catheter distal end 61. (FIG. 6). The catheter 60 further comprises an optional second lumen 65 having a proximal opening 67 at the catheter proximal second end section 63 and a distal opening 57 at or near the distal end 61. The proximal first lumen opening 66 and proximal second lumen opening 67 are offset relative to a catheter proximal end central longitudinal axis 68 (FIGS. 6-9) and have a catheter end face 69 (FIGS. 7-9). The catheter proximal second end section 63 is detachably inserted (step 135) between the spaced apart catheter first guide 98 and catheter second guide 99 as shown in FIG. 16A.

Figure 16B:
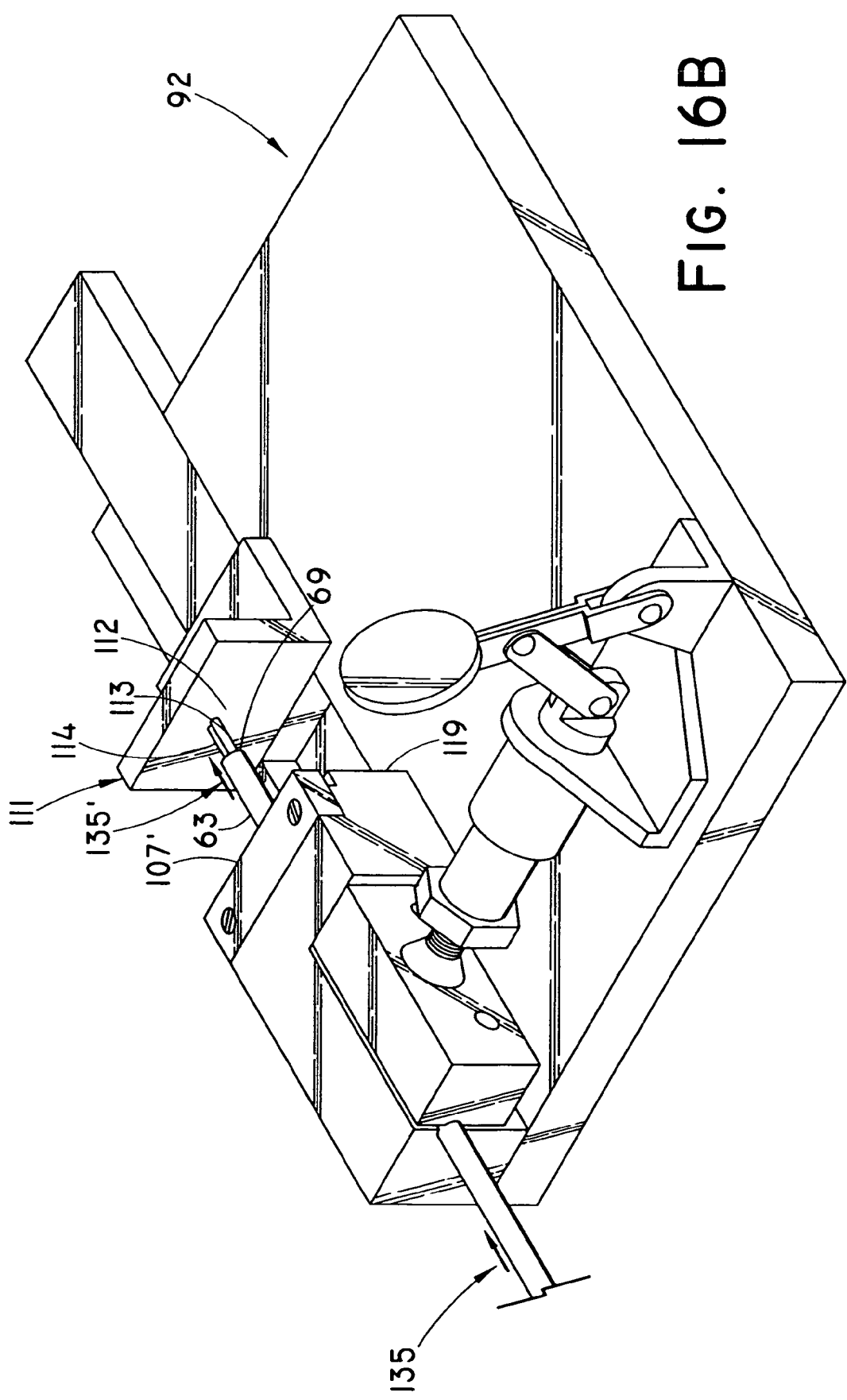
FIGS. 16B and 16C illustrate a schematic diagram of the catheter of FIG. 16A being secured to the jig shown in FIG. 16 according to one embodiment of the present invention.
Figure 16C:
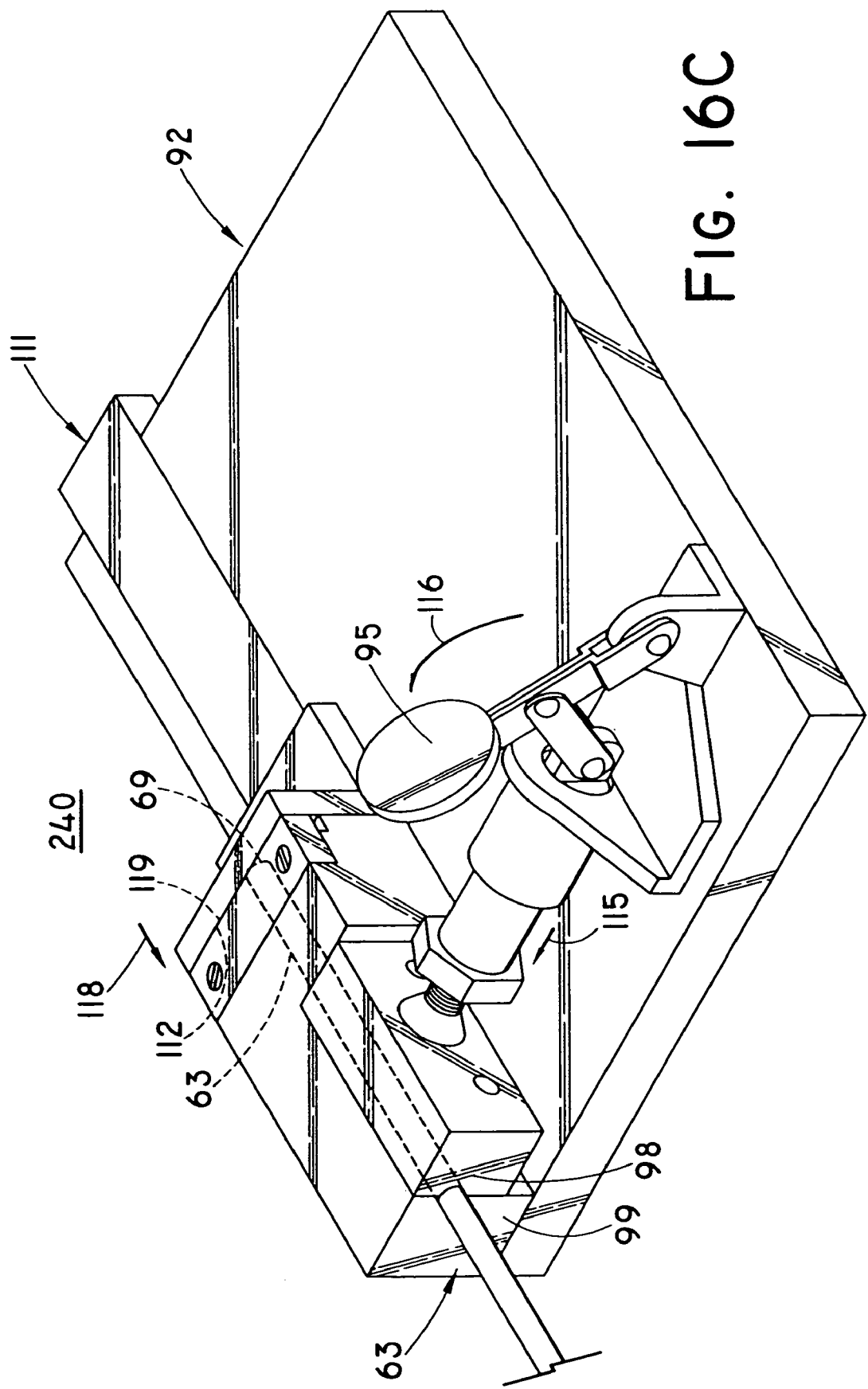

FIGS. 16B and 16C illustrate a schematic diagram of the catheter of FIG. 16A being secured to the jig shown in FIG. 16 according to one embodiment of the present invention. The catheter proximal second end section 63 is optionally detachably disposed over (step 135') the catheter first lumen alignment pin 113 (and optionally the catheter second lumen alignment pin 114) at a position distal the optional catheter guide distal slide face 119 and spacer plate distal slide face 106', wherein the faces 119 and 107' in one embodiment are substantially flush to each other. Optionally, the catheter proximal second end section 63 is disposed over (step 135') the pins 113, 114 until it abuts the proximal face plate 112 of the optional slide plate 111.

The catheter proximal second end section 63 is secured (step 240) by the jig 92 for cutting. The securing step (step 240) may be any step (or series of steps discussed below) whereby the catheter proximal second end section 63 is held between the catheter first and second guides 98, 99, respectively, so as to ensure that the catheter proximal second end section 63 does not pull out from between the guides or shift unintentionally. Several embodiments of the securing step 240 (or series of securing steps) will now be discussed, either of which may be sufficient in and of itself and, where multiple securing steps are performed those steps need not be sequential.

By way of example and not by way of limitation and using the illustrative jig 92 shown in FIG. 16C, according to one embodiment of the invention the securing step 240 comprises the catheter first and second guides 98, 99, respectively, being joined together (step 115) (see FIGS. 15 and 16C), but due to the size of the catheter the joining step does not necessarily mean that the catheter first and second guides 98, 99 will touch each other although they should engage (e.g., abut, touch) the catheter proximal second end section 63. Joining 115 may be done simply by moving by hand the catheter first guide 98 along the axis of the catheter second guide guiding pin 103 that was inserted into the catheter first guide aperture 104 until the catheter first guide groove 101 nearly abuts the catheter second guide groove 102. Because the diameter formed by abutting grooves 101, 102 is slightly less than the catheter proximal second end section 63 to be clamped within the grooves, the catheter first and second guides 98, 99 optionally are slightly spaced apart such that the grooves 101, 102 may receive the catheter proximal second end section 63.

The securing step 240 may also comprise the catheter proximal second end section 63 being inserted (step 135) between the following: the catheter first and second guide grooves 101, 102, respectively, between the spacer plate groove 108 and the distal catheter groove 106 of the catheter second guide 99, and flush with or optionally distal to the spacer plate distal slide face 107' and the catheter second guide distal slide face 119 (FIGS. 15-16B). The catheter proximal second end section 63 is positioned (step 118 in FIGS. 16B and 16C) for cutting such as by a positioning member (e.g., a slide plate 111). For example, the slide plate 111 positions (step 118 in FIGS. 16B and 16C) the catheter proximal second end section 63 by moving toward the catheter proximal second end section 63, the catheter first lumen alignment pin 113 inserting (if it has not already been inserted by another step) into the first lumen 64 and optionally a catheter second lumen alignment pin 114 inserted into the catheter lumen second lumen 65, such that the catheter end face 69 abuts the face plate 112 (FIG. 16C), and the face plate 112 abuts the catheter second guide distal slide face 119 (FIG. 16C). As a result of one embodiment of the positioning step 118, the catheter end face 69 is substantially flush with the catheter second guide distal slide face 119. In one embodiment, the securing step 240 also comprises actuating (step 116) the lever 95 to clamp (step 117) the catheter first and second guide grooves 101, 102, respectively, about the catheter proximal second end section 63 sufficient to tighten the catheter first and second guides 98, 99, respectively, about the catheter proximal second end section 63, which cannot easily pull out from between the guides or shift unintentionally. Optionally, actuating (step 116) pushes the screw 96 (FIG. 15) against the catheter first guide 98 and thereby moving the catheter first guide 98 farther toward the catheter second guide 99.

Figure 16D:
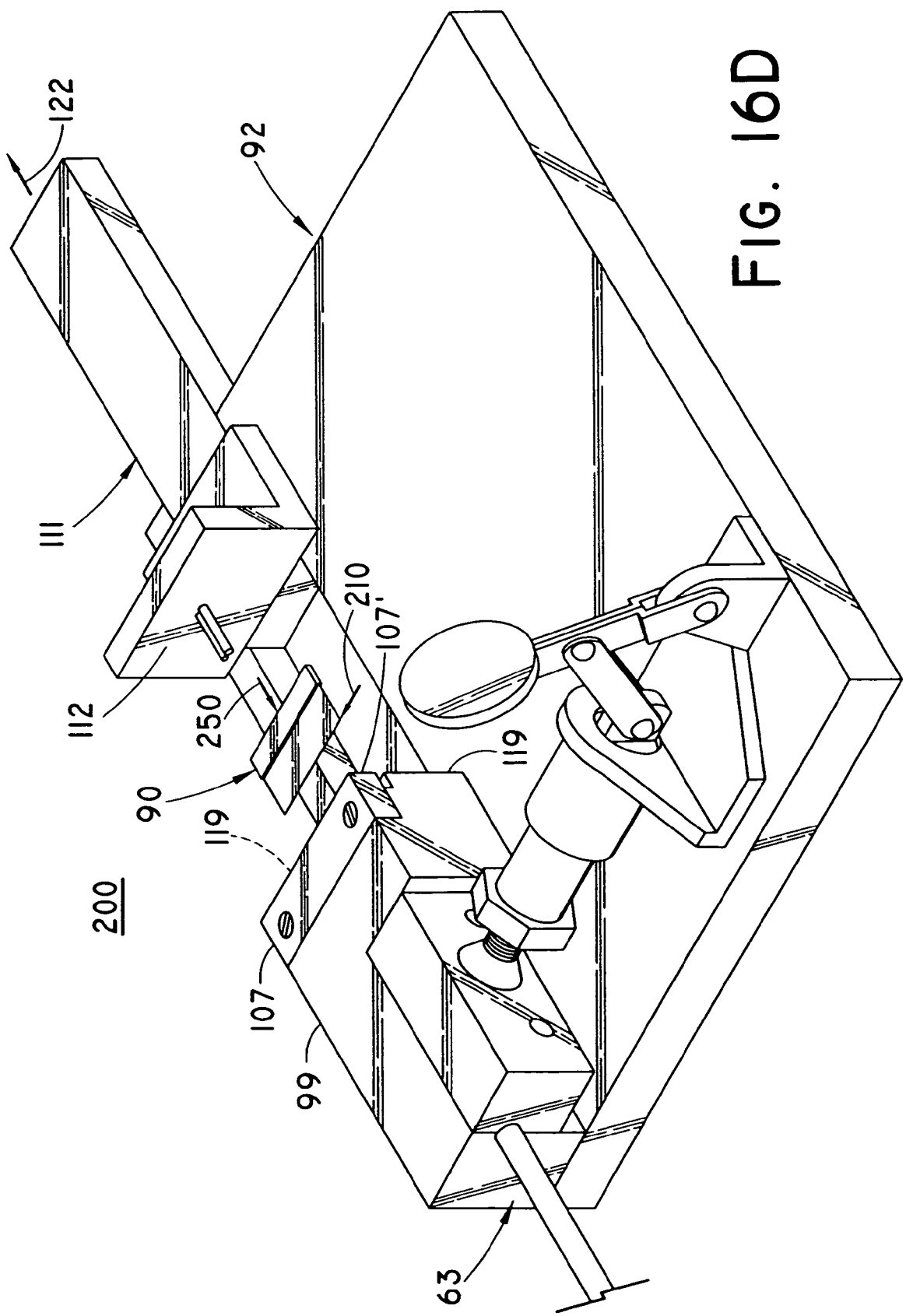
FIG. 16D shows a schematic diagram of a cutting step of the catheter according to one embodiment of the present invention.

FIG. 16D shows a schematic diagram of a cutting step (step 250) of the catheter according to one embodiment of the present invention. The positioning member (e.g., the slide plate 111) is withdrawn (step 122) to allow room for the cutting tool 90 to be provided (step 210). In one embodiment by way of example, the slide plate 111 is withdrawn (step 122) so that there is room for providing (step 210) the cutting tool between the proximal face plate 112 of the optional slide plate 111 on the one hand and on the other hand the optional catheter guide distal slide face 119 of the catheter second guide 99 and the distal slide face 107' of the optional spacer plate 107. In one embodiment the positioning member withdrawing step (step 122), the positioning member (e.g., the slide plate 111 is moved in the opposite direction of the positioning step 118 (FIG. 16C).

The cutting tool 90 cuts (step 250) the catheter proximal second end section 63. The cutting step (step 250) further comprises the spacer plate 107 and the catheter second guide 99 being spaced apart by the slot 123 that is configured to receive the cutting edge 91 of the cutting tool 90 and corresponding to the length 76 of the catheter proximal second end section 63 to be cut into the at least two tails 72, 74, wherein the cutting step (step 250) moves the cutting edge 91 into the slot 123. More particularly, the cutting edge 91 of the tool 90 during the cutting step 250 cuts across end face 69 of the proximal second end section 63 (see, e.g., FIGS. 6-9, 16B, 16C) and at least one of the first and second catheter lumens 64, 65, respectively (see, e.g., FIGS. 7-13A), and at least one of the corresponding first and second lumen openings 66, 67, respectively (see, e.g., FIGS. 7-13A).

Figure 16E:
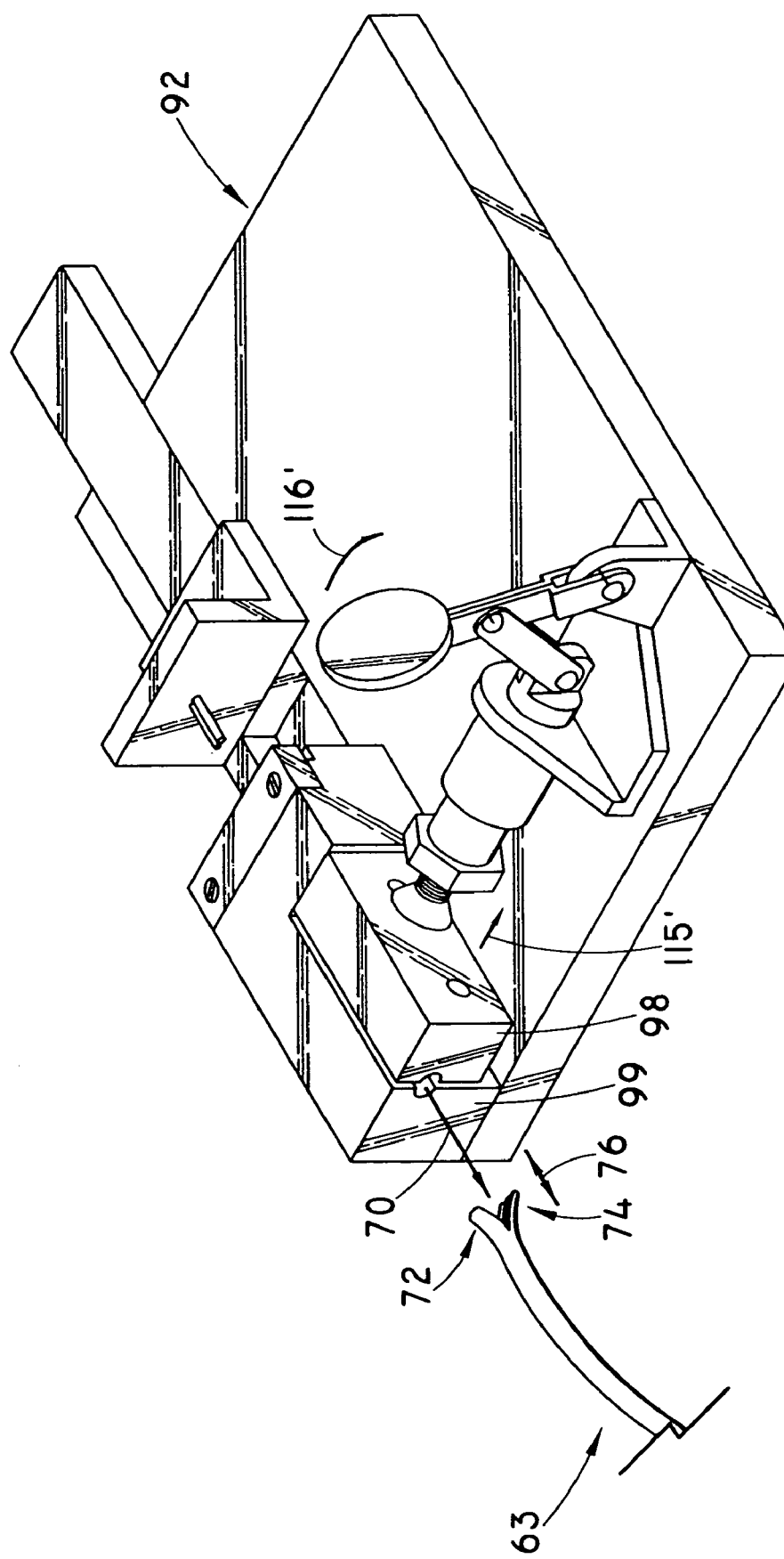
FIG. 16E illustrates a schematic diagram of the catheter of FIG. 16D being released from the jig according to one embodiment of the present invention.

FIG. 16E illustrates a schematic diagram of the catheter of FIG. 16D being released from the jig according to one embodiment of the present invention after the cutting step 250. As shown, the cutting step 250 formed a slit 70 at the catheter proximal second end section 63 thereby exposing at least one of the first and second catheter lumens 64, 65, respectively (e.g., FIGS. 10-12). More particularly, the cutting step 250 occurs over a slit length 76, wherein by forming the slit 70 over the slit length 76 the cutting step 250 forms at least a first tail 72 and second tail 74. (FIG. 16E). The length of the tails 72, 74 correspond to the slit length 76 that may vary but in one embodiment the slit length 76 is from about 2.0 mm to about 5.0 mm in length for the reasons previously explained. (FIG. 16E). As shown in FIGS. 10, 11, and 12, each tail has an inner engaging surface (e.g., 78, 80, 84, 86), an outer engaging surface (e.g., 82, 88), and at least one peripheral engaging surface (e.g., 87, 87'). By way of example only and not by way of limitation, the cutting edge 91 inserts into the slot 123 (FIG. 15) and to a depth of the catheter second guide step 124 (FIG. 15) or optionally to a depth of the catheter second guide slit stop 109 (FIG. 15) either of which correspond to the slit length 76. The cutting tool may be removed, the lever 95 de-actuated 116' and, thereby, the catheter first and second guides 98, 99, respectively, are separated 115'. (FIG. 16E). Optionally, the catheter tails 72, 74 may need to be peeled apart slightly.

The steps 210, 220, 230, 240, and 250 according to the method 200 of cutting a catheter 60 at the proximal second end 63 to form catheter tails 72, 74 need not be performed sequentially.

It is intended that the foregoing detailed description of methods according to the invention be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

What is claimed is:

1. A luer assembly, comprising:
    a first connector having a first catheter engaging body, a fastener, and a lumen;
    a second connector having a distal first end and a proximal second end, a fastener, a second catheter engaging body, a passageway, and a cavity that accommodates the first connector catheter engaging body;
    a catheter having a distal first end, an elongate middle portion, a proximal second end section comprising an end face, and at least two lumens, such that a first catheter lumen comprises a first proximal opening at the catheter end face and a first distal opening at or near the distal first end of the catheter and defining a first passageway therebetween, and such that a second catheter lumen comprises a second proximal opening at the catheter end face and a second distal opening at or near the distal first end of the catheter and defining a second passageway therebetween; and
    a transverse catheter slit across the proximal second end section first proximal opening of the catheter end face and the first catheter passageway, the catheter slit extends longitudinally for a slit length corresponding to the first and second catheter engaging bodies and sufficient to provide joint integrity and operatively couple the proximal second end section of the catheter between the first connector catheter engaging body and the second connector catheter engaging body,
    wherein the catheter slit exposes at least the first catheter passageway along said catheter slit length and forms at least two tails,
    wherein the catheter proximal second end section is disposed within the second connector passageway such that the at least two catheter tails are disposed between the first connector catheter engaging body and the second connector catheter engaging body and
    wherein the first connector fastener and second connector fastener operatively couple the first connector and the second connector such that the at least two catheter tails are operatively coupled between the first connector catheter engaging body and the second connector catheter engaging body.

2. The device of claim 1 wherein the first connector further comprises a distal insert having a distal first end comprising an opening and a proximal second end comprising an opening, the openings defining a lumen therebetween, and the insert distal first end being at least partially inserted within the first catheter passageway at the catheter proximal second end section such that the first connector lumen, the insert lumen and the catheter passageway are in fluid communication.

3. The device of claim 2 wherein the first connector distal insert further comprises a fastener at or near the insert proximal second end, the insert fastener engaging the catheter proximal second end section within the catheter passageway.

4. The device of claim 1 wherein the first tail comprises a first inner engaging surface, a peripheral engaging surface, and an outer engaging surface, and the second tail comprises a first inner engaging surface, a peripheral engaging surface, and an outer engaging surface.

5. The device of claim 1 wherein the first tail inner engaging surface and second tail inner engaging surface are disposed about the first connector catheter engaging body and the first tail outer engaging surface and second tail outer engaging surface are disposed about the second connector catheter engaging body.

6. The device of claim 1 wherein the transverse catheter slit is across the catheter's proximal second end section second proximal opening and the second catheter passageway such that the first tail further comprises a second inner engaging surface and an interstitial engaging surface positioned between the first and second inner engaging surfaces and such that the second tail further comprises a second inner engaging surface and an interstitial engaging surface positioned between the first and second inner engaging surfaces.

7. The device of claim 1 wherein the first connector comprises a male luer fitting connector and the second connector comprises a female luer fitting connector.

8. A method for attaching a catheter to a luer assembly, the method comprising the steps of:
   providing a first connector having a first catheter engaging body, a fastener, and a lumen;
   providing a second connector having a distal first end and a proximal second end, a fastener, a second catheter engaging body, a passageway, and a cavity that accommodates the first connector catheter engaging body;
   providing a catheter having a distal first end, an elongate middle portion, a proximal second end section comprising an end face having a cross section, an opening at the end face and an opening at or near the distal first end defining a lumen therebetween, and a transverse catheter slit across the proximal second end section opening of the catheter end face and the catheter lumen, the catheter slit extends longitudinally for a slit length corresponding to the first and second catheter engaging bodies and sufficient to provide joint integrity and operatively couple the proximal second end section of the catheter between the first connector catheter engaging body and the second connector catheter engaging body, the catheter slit exposes at least one catheter lumen along said length and forms at least two tails, the catheter proximal second end section being disposed within the second connector passageway such that the catheter tails are disposed between the first connector catheter engaging body and the second connector catheter engaging body; and
   operatively coupling the first connector fastener and second connector fastener such that the catheter tails are operatively coupled between the first connector catheter engaging body and the second connector catheter engaging body.

9. The method of claim 8 further comprising an inserting step wherein the first connector comprises a distal insert having a distal first end and a proximal second end and the inserting step comprises inserting the distal first end into the catheter lumen.

10. The method of claim 9 wherein the inserting step further comprises the insert proximal second end having a fastener and the inserting step comprises inserting the distal first end fastener within the catheter lumen such that the insert proximal second end fastener engages the catheter proximal second end section.

11. The method of claim 8 further comprising the step of disposing the catheter first tail and second tail about the first connector catheter engaging body.

12. The method of claim 11 wherein the disposing step includes catheter tails comprising inner engaging surfaces, peripheral engaging surfaces, and outer engaging surfaces and the disposing step comprises disposing at least one of the inner and peripheral engaging surfaces about the first connector catheter engaging body.

13. The method of claim 12 wherein the disposing step further comprises disposing the catheter tail outer engaging surfaces about the second connector catheter engaging body.

14. The method of claim 8 further comprising the step of moving the second connector over the first connector catheter engaging body such that the second connector catheter engaging body and first connector catheter engaging body may operatively couple the catheter tails therebetween.

15. The method of claim 8 wherein operatively coupling the fasteners comprises rotating at least one of the first and second connectors relative to the other.

16. The device of claim 1 wherein the slit length is at least about 2.0 mm and less than about 5.00 mm.

17. The device of claim 1 wherein the catheter length is from about 50 centimeters to about 600 centimeters.

\* \* \* \* \*

UNITED STATES PATENT AND TRADEMARK OFFICE
CERTIFICATE OF CORRECTION

| | | |
|---|---|---|
| PATENT NO. | : 7,601,147 B2 | Page 1 of 1 |
| APPLICATION NO. | : 11/645324 | |
| DATED | : October 13, 2009 | |
| INVENTOR(S) | : F. Waller et al. | |

It is certified that error appears in the above-identified patent and that said Letters Patent is hereby corrected as shown below:

On the Title Page

Item (73), replace "Winston-Cook Medical Inc." with --Wilson-Cook Medical Inc.--.

Signed and Sealed this
Third Day of May, 2011

David J. Kappos
*Director of the United States Patent and Trademark Office*